United States Patent
Hang et al.

(10) Patent No.: US 12,280,078 B2
(45) Date of Patent: *Apr. 22, 2025

(54) MODIFIED MICROORGANISMS EXPRESSING SAGA AND RELATED COMPOSITIONS FOR IMMUNOMODULATION AGAINST INFECTION AND CANCER IMMUNOTHERAPY

(71) Applicant: THE ROCKEFELLER UNIVERSITY, New York, NY (US)

(72) Inventors: Howard Hang, Del Mar, CA (US); Matthew Griffin, New York, NY (US)

(73) Assignee: THE ROCKEFELLER UNIVERSITY, New York, NY (US)

(*) Notice: Subject to any disclaimer, the term of this patent is extended or adjusted under 35 U.S.C. 154(b) by 757 days.

This patent is subject to a terminal disclaimer.

(21) Appl. No.: 17/432,500

(22) PCT Filed: Feb. 20, 2020

(86) PCT No.: PCT/US2020/019038
§ 371 (c)(1),
(2) Date: Aug. 20, 2021

(87) PCT Pub. No.: WO2020/172406
PCT Pub. Date: Aug. 27, 2020

(65) Prior Publication Data
US 2022/0168364 A1    Jun. 2, 2022

Related U.S. Application Data

(60) Provisional application No. 62/807,830, filed on Feb. 20, 2019.

(51) Int. Cl.
| | | |
|---|---|---|
| *A61K 35/747* | (2015.01) | |
| *A23C 9/123* | (2006.01) | |
| *A23K 10/18* | (2016.01) | |
| *A23L 33/135* | (2016.01) | |
| *A61K 45/06* | (2006.01) | |
| *A61P 35/00* | (2006.01) | |
| *C07K 14/315* | (2006.01) | |
| *C12N 9/14* | (2006.01) | |

(52) U.S. Cl.
CPC .......... *A61K 35/747* (2013.01); *A23C 9/1234* (2013.01); *A23K 10/18* (2016.05); *A23L 33/135* (2016.08); *A61K 45/06* (2013.01); *A61P 35/00* (2018.01); *C07K 14/315* (2013.01); *A23V 2002/00* (2013.01); *A23V 2400/157* (2023.08); *A23V 2400/169* (2023.08)

(58) Field of Classification Search
CPC .... A61K 35/747; A61K 45/06; A61K 35/744; A23C 9/1234; A23K 10/18; A23L 33/135; A61P 35/00; C07K 14/315; A23V 2002/00; A23V 2400/157; A23V 2400/169; C12N 9/14; C12N 15/746
See application file for complete search history.

(56) References Cited

U.S. PATENT DOCUMENTS

| | | |
|---|---|---|
| 6,583,275 B1 | 6/2003 | Doucette-Stamm et al. |
| 10,723,771 B2 | 7/2020 | Hang et al. |
| 2004/0029129 A1 | 2/2004 | Wang et al. |
| 2012/0121638 A1 | 5/2012 | Huebner et al. |

FOREIGN PATENT DOCUMENTS

| | | |
|---|---|---|
| WO | WO 99/49049 | 9/1999 |
| WO | WO 01/07083 | 2/2001 |
| WO | WO 2016/172476 | 10/2016 |

OTHER PUBLICATIONS

Written Opinion in International Application No. PCT/US2020/019038, May 27, 2020, pp. 1-6.
Rangan, K. J. et al. "A secreted bacterial peptidoglycan hydrolase enhances tolerance to enteric pathogens" *Science*, Sep. 23, 2016, pp. 1-15, vol. 353, No. 6306.
Pedicord, V. A. et al. "Exploiting a host-commensal interaction to promote intestinal barrier function and enteric pathogen tolerance" *Sci Immunol.*, Sep. 2016, pp. 1-29, vol. 1, No. 3.
Ogawa, C. et al. "Muramyl dipeptide and its derivatives: peptide adjuvant in immunological disorders and cancer therapy" *Curr Bioact Compd.*, Sep. 2011, pp. 1-37, vol. 7, No. 3.
Extended European Search Report for Application No. EP 20759985.3, Oct. 11, 2022, pp. 1-7.

*Primary Examiner* — Satyendra K Singh
(74) *Attorney, Agent, or Firm* — SALIWANCHIK, LLOYD & EISENSCHENK

(57) ABSTRACT

Provided are compositions and methods based in part on the discovery that *Enterococcus faecium* secreted antigen A (SagA)-expressing bacteria are protective against enteric infections and enhances immune checkpoint inhibitor efficacy against cancer. Bacteria that express SagA or heterologous SagA, or orthologs thereof, are provided, and are included as nutraceutical, pharmaceutical, and probiotic formulations, as well as components of food products, including dairy products.

7 Claims, 16 Drawing Sheets

Specification includes a Sequence Listing.

| Species | Strain | NCBI Ref. Seq. ID | Uniprot (Uniparc) ID | BioCyc ID |
|---|---|---|---|---|
| *Enterococcus durans* | IPLA 655 | WP_005875163.1 | W1KC53_9ENTE | G10WH-1540 |
| *Enterococcus hirae* | ATCC 9790 | WP_010737285.1 | I6SXE0_ENTHA | GLCW-1122 |
| *Enterococcus mundtii* | QU25 | WP_023520500.1 | V5XRV1_ENTMU | G1HM7-2713 |
| *Enterococcus raffinosus* | DSM 5633 | WP_010745322.1 | A0A1L8X204_9ENTE | G1FDO-3672 |
| *Enterococcus gilvus* | ATCC BAA-350 | WP_010779611.1 | R2XR41_9ENTE | G17M5-2733 |
| *Enterococcus villorum* | ATCC 700913 | WP_010750171.1 | R2QCG9_9ENTE | N/A |
| *Enterococcus ratti* | DSM 15687 | WP_071854587.1 | (UPI000789B852) | N/A |
| *Enterococcus cecorum* | ATCC 43198 | WP_016250555.1 | S1R077_9ENTE | N/A |
| *Enterococcus phoeniculicola* | ATCC BAA-412 | WP_010766937.1 | R3WNY7_9ENTE | G17M4-3390 |
| *Enterococcus saccharolyticus* | ATCC 43076 | WP_016173829.1 | S0JBL9_9ENTE | N/A |
| *Enterococcus columbae* | ATCC 51263 | WP_016184361.1 | S1P5S6_9ENTE | G17LZ_2240 |
| *Enterococcus hermanniensis* | DSM 17122 | WP_071858063.1 | A0A1L8TMZ2_9ENTE | RV04_GL002208 |
| *Enterococcus devriesei* | DSM 22802 | WP_071863006.1 | (UPI0008FFF9F3) | G1FDN-662 |
| *Enterococcus malodoratus* | ATCC 43197 | WP_010741104.1 | R2NX64_9ENTE | G17M1-4401 |
| *Enterococcus avium* | FDAARGOS_182 | WP_049219848.1 | (UPI0006651D4C) | N/A |
| *Enterococcus casseliflavus* | ATCC 25788 | WP_060793036.1 | A0A377MJZ6_ENTCA | N/A |
| *Enterococcus gallinarum* | FDAARGOS_163 | WP_061054362.1 | A0A0X8PRZ6_ENTGA | G1BQV-3235 |

FIG. 1

| Species | NCBI Ref. Seq. | Sequence |
|---|---|---|
| *Enterococcus faecium (Efm)* | N/A | MKKSLISAVMVCSMTLTAVASPIAAAADDFDSQIQQQD QKIADLKNQQADAQSQIDALESQVSEINTQAQDLLAKQD TLRQESAQLVKDIADLQERIEKREDTIQKQAREAQVSNTS SNYIDAVLNADSLADAIGRVQAMTTMVKANNDLMEQQ KQDKKAVEDKKAENDAKLKELAENQAALESQKGDLLS KQADLNVLKTSLAAEQATAEDKKADLNRQKAEAEAEQ ARIREQQRLAEQARQQAAQEKAEKEAREQAEAEAQATQ ASSTAQSSASEESSAAQSSTTEESSSAAQSSTTEESTTAPE SSTTEESTTAPESSTTEESTTVPESSTTEESTTVPESSTTEES TTVPESSTTEESTTVPETSTEESTTPAPTTPSTDQSVDPGN STGSNATNNTTNTTPTPTPSGSVNGAAIVAEAYKYIGTPY VWGGKDPSGFDCSGFTRYVYLQVTGRDIGGWTVPQESA GTKISVSQAKAGDLLFWGSPGGTYHVAIALGGGQYIHAP QPGESVKVGSVQWFAPDFAVSM (SEQ ID NO: 1) |
| *Enterococcus durans (Edr)* | WP_005875163.1 | MKKSLISAVMLSSIALTAVGSPIAAAADDFDSQIQQQDQ KIADLQNQQASAQSQIEALEGQVSSINAKAQDLLTKQDT LRKESSQLEKEIADLQERIEKREATIQKQARETQVKNTSS NYIDAVLNADSLADAVGRIQAMTSIVKANQDLVDQQKQ DKQAVEDKKAENEAKQKELSANQATLESQKGDLLAKQ ADLNVLKTSLAAEQATAEDKKADLNRKKAEAEAEQARI REQARLAEQARQQAAQEKAEKEAREQAAAQAAQSQAA QSQAASSASTTENSSTVQSSTTENSSSSAQSSSSSSSAVVT PGSSSTTEESTVPESSTSTTENSSTESSTTDSSVTESTTVPE SSTQETTPATPTTPSTPATSNNGSTGNGGTPNNTGTVVTP PTTPSTPSGSVNGSAIVAEAYKYIGVPYVWGGKDPSGFD CSGFTSYVYKQVTGRDIGGWTVPQENAGAKISVSQAKA GDLLFWGSPGGTYHVAIALGGGQYIHAPQPGESVKVGS VQWFAPDFAVSM (SEQ ID NO: 2) |
| *Enterococcus hirae (Ehr)* | WP_010737285.1 | MKKSLLSAVMLSSIALTAVGSPIAAAADDFDSQIQQQDK KIADLQNQQASAQSQIEALEGQVSAINTKAQDLLTKQDT LRKESAQLKQEIKDLQERIEKREATIQKQARETQVKNTSS NYIDAVLNADSLADAVGRIQAMSTIVKANQDLVQQQKE DKQAVEAKKAENEAKQKELADNQAALESQKGDLLAKQ ADLNVLKTSLAAEQATAEDKKADLNRKKAEAEAEQARI REQARLAEQARQQAAQEKAEKEAREQAAAQAAQTQAL SSASTTTESSSAAQSSSEESKAPESSTTEESTSTESSTTTEN SSTGSSSTESSSTEESTVPESSTQESTPANTESSSSSSNTNV NNNTNNSTNNSTNNSTTNNNNNNNTVTPAPTPTPTPAPA PAPNPSGSVNGAAIVAEAYKYIGTPYVWGGKDPSGFDCS GFTRYVYLQVTGRDIGGWTVPQESAGTKISVSQAKAGD LLFWGSAGGTYHVAISLGGGQYIHAPQPGENVKVGSVQ WYTPDFAVSM (SEQ ID NO: 3) |

FIG. 2

| | | |
|---|---|---|
| *Enterococcus mundtii* (Emn) | WP_023520500.1 | MKKSLISAVMVSSMALTAVASPIAAAAEDFDSQIQQQDQ KIAELQNQQASAQSQIEALEGQVADINTKAETLLANQAT LRQESSQLTQEIADLQERIEKREATIQEQARETQVKGTSS NYIDAVLNAESFSDAIGRVQAMSSIVRANQDLVKQQKED KQAVEDKKAENEAKLQELAENQAALESQKGDLLSKQA DLNVLKTTLAAEQATAEDKKEDLNRQKAEAEAEQARIR EQARLAEQARQQAAQEQAEREAREQAAVAAAAAQEQE QASSSSVQESTEVSESATSESSSSAESSTEQSSVPESSTSTE DSTTESSVPESSTEESTTTPSVPETTTPSTPEPSTPAPSTPEP STPAPSTPAPSTPEPSTPAPSIPAPTAPSTNGAAIVAEAMK YIGTPYVWGGKDPSGFDCSGFTRYVYLQVTGRDIGGWT VPQESAGARISVSQAKAGDLLFWGAAGGTYHVAISLGG GQYIHAPQPGESVKIGSVQWYAPDFAVSM (SEQ ID NO: 4) |
| *Enterococcus raffinosus* (Erf) | WP_010745322.1 | MKKSLLSALMVCSVTLSALAAPAAASADEFDSKIADQD AKISSLQNQQTDAQSQISALEGEVASINEKAQGLLNEQAS LRQESQDLQKQIETLQKRIEKRSEAIKEQARDTQVKQSSG TNVIDVVLNAESFTDAVSRVQAMTTIVKANNDLVEQQK ADKAEVEQKQAENKKQQEQIAANQATLESQKGELITKQ ADLNVQTTTLAAEQATAEGEKASLKEKQEAAIKEQERV QEEARKAAEAQEAAKKADADAKAKADADAKAEADRK AQEEAAASTTTTESSTVESSSTVESSTTEQQTQSSATESSS TASSSEDNFQGGGATPTPSTTEDSGSSNQGSTSSSTNNNQ TPSTPTPAPTPTPAPAPSGNTGGVVAEAMKYIGTPYVWG GKTPAGFDCSGFTSYVYRQATGREIGGWTVPQESAGTRI SVDQAQAGDLYFWGSPGGSYHVAIAMGGGQYIHAPQPG ETVTVSSVSYYAPSFAVRM (SEQ ID NO: 5) |
| *Enterococcus gilvus* (Egv) | WP_010779611.1 | MKKSLLSALMVCSVTLSALAAPAAASADEFDSKIADQD AKISSLQNQQTDAQSQISALEGEVASINDKAQGLLNEQA SLKQKSQELQKQIETLDKRIEKRSEAIKEQARSAQVKQSS GSNVVDVVLNAESFTDVVSRVQAMATIAKANNDLVEQ QKADKAEVEQKQSENQKQLEQIAANQATLESQKGDLIT KQADLNVQTTTLAADQATAEGEKASLKEKQDAAIKEQQ RVQEEARKAAEAQEAAKKAETDAKAKADADAKAEADR KAQEEAAASTTTTESSTVESSTTVETSSTEQQTSTTESSSS ESSSEDNFQGGGATPTDNGNSSANNNQGSTSSSTNDQTP APTPTPAPEVPKPSTPTPPPATSGSVVAEAMKYIGTPYVW GGKTPAGFDCSGFTSYVFRQATGREIGGWTVPQESAGTR ISVGEAQAGDLYFWGSPGGTYHVAIAMGGGQYIHAPQP GETVTVSSVSYYAPSFAVRM (SEQ ID NO: 6) |
| *Enterococcus villorum* (Evl) | WP_010750171.1 | MKKSLLSAVMLSSIALTAVGSPIAAAADDFDSQIQQQDK KIADLQNQQLSAQSQIEALEGQVSAINTKAQDLLAKQDT LRKESTQLKKEIADLQERIEKREATIQKQARETQVKNTSS NYIDAVLNADSLADAVGRIQAMSSIVKANQDLVQQQKE DKQAVEAKKAENEAKQKELAENQAALESQKGDLLAKQ ADLNVLKTSLAAEQATAEDKKADLNRKKAEAEAEQARI REQARLAEQARQQAAQEKAEKEAREQAAAQAALSQAT STTESSSTVSSSTTESSSVAQSSSEESTTSESSTTTTEESTTS ESSTTTTEESTVPESSTTTENSSTDSSTTESSVTESSTVPES STQDSTTSTNTSNSNNSNNATTPTTPSTPSTPSGSVNGAAI VAEAYKYIGTPYVWGGKDPSGFDCSGFTRYVYLQVTGR DIGGWTVPQESAGAKISVSQAKAGDLLFWGSPGGTYHV AIALGGGQYIHAPQPGENVKVGSVQWYAPDFAVSM (SEQ ID NO: 7) |

FIG. 2 (continued)

| Enterococcus ratti (Ert) | WP_071854587.1 | MKKSLLSAVMLSSIALTAVGSPIAAAAEDFDSQIQQQDK KIADLQNQQSSAQAQIEALEDQVSTINAQAQDLLAKQAT LRKESAQLKQEIADLQERIEKREATIQKQARETQVKNTSS NYIDAVLNADSFADAIGRIQAMSSIVKANQELVQQQKED KQAVEAKKNENEAKQKELAKNQAVLESQKGDLLAKQA DLNVLKTSLAAEQATAEGKKAELNRKKAEAQAEQARIR EQARLAEQARQQAAREKAEKEAREQAAAQTKASTTEDS SVAQSSSQESAASESSTTSTEGSSTANSSTTAENSSTGSSS SESSVTDESTISDSSTSDSTPATDSGSSNSSSSNNAGNTSD SSSDSSNPTGDSSTSNDTNNTNNSDNAVVPTPAPSQPAGS VNGSSIVAEAYKYIGVPYVWGGKDPSGFDCSGFTRYVY LQATGRDIGGWTVPQESAGTRISVSQAKAGDLLFWGSPG GSYHVAISLGGGQYIHAPQPGESVKVGSVQWFAPDFAVS M (SEQ ID NO: 8) |
|---|---|---|
| Enterococcus cecorum (Ecc) | WP_016250555.1 | MVKKRLSSVVIVSTVLAGTLVAPIATFADNYDSQIEQKN SEINDLKSKQSEAQDQIDRLETSINKINKKADELLKEQST LREETVQLQKDIEVLTERIAKREEAIRNQARDVQVNNQS SVYVKALLDATSFTDALGRLKAMTTIVNANNDLVNQQK ADKKAVEDKKAENEAKQEEIAKNQATLEEQKGTLEAKQ ADLNVLKASLAEQQATKESEKQALAEQKAAFEAEQKRV REQQAQAAAVQQAAQQAQASASTSSNAAASTNSNAGSS SSQASSSNSASSNASSSNAGVSNVVIPSRPAPAPSGNGSAI VAEAYKHIGKPYVWGAKGPNTFDCSGFTRYVYLQVTGR DIGGWTVPQEGAGAIIPVSQAQPGDLYFWGSRGSSYHVA IALGGGSYIHAPQPGESVKVGSVAYFAPSFAVRM (SEQ ID NO: 9) |
| Enterococcus phoeniculicola (Eph) | WP_010766937.1 | MKKSLLSTVMICSLTLTTLASPLVATADNLDDQIAQQNQ KISELQGQQADVQAQISSLQAEVDTINGKAEDLLAKQKE LYTKSDELKTEIKNLQERIEKREEAITDQARDVQVNGGSS NFIDAVLNADSFTDAIGRVQAMNTIVQANNDLVEQQKQ DKADVEAKEAENKKQLEEIAANQAELENQKGVLTEKQA DLNVLTTTLAAEQATAEGKKSDLNKQEAAIAEQARVQ AEAKKAEEVKAAAAAEKEKAEAEQAVTPVTETQTSGNT QNVVNNDEPAKVPETPAANSNTTSNTTPNTTPDTTPAEE KPVTPTPAPSGNGSSVVAEAYKYIGTPYVWGGKDPSGFD CSGFTSYVYRQATGREIGGWTVPQESAGAKIGINEAQAG DLLFWGSPGGTHHVAIALGGGQYIHAPQPGESVKIGSYQ WYAPDFAVRM (SEQ ID NO: 10) |
| Enterococcus saccharolyticus (Esc) | WP_016173829.1 | MKKRVLTALLTCSLTLTAVAAPVAVFADDFDQQIEQKN KEISDLQAQQASIQDQISSLEGQISDINTKAEELIAKQQEL AAQSQKLQEEIADLEVRIEKREEAIRKQARDVQVNGSDS NLVEAVLNADSLTDAIGRVQAMSTIVNANNELVNQQKE DKKAVETKKAENEAKQQEIAENQTALEAQKGEIQRSQA DLDYLKADLALQQSSKEDEKKGIQKRKAEAEAERARIAE QERLAELARKAAAEAAAKQAQVEKEAQEAAKEQQAQV SSQEQVQQSTPATEAVAESTTEAPVANATSEEPAAVETP AETNQNTTQDTPTSTPVVEEKTVESTPVQEVVETPTVETP APVEQTPVVETPKVETPKVESSAPTGSVVAEAYKYIGVP YVWGGKDPSGFDCSGFTSYVYRKATGREIGGWTVPQES AGSVISVSEAKAGDLLFWGSQGSTYHVAIALGGGQYIHA PAPGQSVTVASVAYFAPSFAVSM (SEQ ID NO: 11) |

FIG. 2 (continued)

| | | |
|---|---|---|
| *Enterococcus columbae* (Ecb) | WP_016184361.1 | MKKRLSSVVIASTVLLGTLTAPMVAMADNYDTQIEQKN SEINDLKAKQSSAQKQIDELEASVAKINKQANELLDQQA TLQDESVQLQKDIETLKERIAKREETIQRQARDVQEKNQ SSVFIKALLDADSFSDALGRLKAMTTIVNANNDLVNQQK ADKKAVEDKKAENEKKQAEIAANQAKLEEQKGTLEAK QADLNVLKSTLAAQQATKESEKEALNAQKAAYEAEQA RIRQEQAQVAATRQAVAQQASSSQASASASNTGSSSSSA SVSTPAVSIPSTPAPAPSGNGSAIVAEAYKHIGKPYVWGA KGPDTFDCSGFTRYVYLQVTGRDIGGWTVPQESAGTVIP VSQAQPGDLYFWGSRGSTSHVAIAIGGGQYIHAPQPGET VKVGSVAYFAPSFAVRM (SEQ ID NO: 12) |
| *Enterococcus hermanniensis* (Ehm) | WP_071858063.1 | MKKSLLSALMVCSVTLSALAAPAAASADEFDSKIADQD AKISSLQNQQTDAQSQISALENEVAAINDQAQSLLNNQA SLRQKSQDLENQINALQKRIEKRSEAIKEQARNVQVKQS STNVIDVVLNAESFSDAVGRVQAMSTIVKANNDLVEQQ KADKAEVEQKQAENKKQQEAIVANQSALESQKGDLITK QADLNVQTTTLAAEQATAENEKADLQAKQEAAIKEQQR VQEEARQAAAAQEAAQKAEAERQAQADAKAQEEAASS ESSTQASTEASTTTVESSTTQESTESSSTTTVESSSTEQTAPS TSTTDSSTTTESSTATTEDSSQATEVTPPASSTDTSTSTSN SSNQESSTSTNTSTSTNNSSNQGSSTSTGNSNQGSTSSSND QTATTPSTPSTSTPAPSGNGAAVVAEAMKYIGTPYVWGG KTPSGFDCSGFTAYVYRQATGREIGGWTVPQESAGTRIS VSEAQAGDLYFWGSPGGSYHVAIAMGGGQYIHAPQPGE SVKVGSTAYYAPSFAVRM (SEQ ID NO: 13) |
| *Enterococcus devriesei* (Edv) | WP_071863006.1 | MKKSLLSALMVCSVTLSALAAPAAASADEFDSKIADQD AKISSLQNQQTDAQSQISALEGEVASINDKAQSLLNEQAT LRQKSQDLQKQIKTLQERIEKRSEAIKEQARDVQVKQSS TNVIDVVLNAESFSDAVGRVQAMSTIVKANNDLVEQQK ADKVEVEQKQAETQKQQEQITANQAALESQKGDLITKQ ADLNVQTTTLAAEQATAEGEKANLKDKQAAAIQEQQRV QEEAKKAAEAQEAAQKAEVERQAKADADAKAEADRK AQEEAAASASSTESSTVESSTTEASSTEQTTQSSTVESSTG STSEDNFQGGGVTPTPTPPSTTPETPTNNENSNSGNQGSN QTPAPTPTPTPTPEPTPAPTPTPAPSGNTAGVVAEAMKYI GTPYVWGGKTPAGFDCSGFTSYVFRQATGREIGGWTVP QESAGTRISVSQAQAGDLYFWGSPGGSYHVAIAMGGGQ YIHAPQPGQSVTVSSVSYFAPSFAVRM (SEQ ID NO: 14) |
| *Enterococcus malodoratus* (Eml) | WP_010741104.1 | MKKSLLSALMVCSVTLSALAAPAAASADEFDSKIADQD AKISSLENQQTDAQSQINALEGEVASINDKAQGLLNEQA SLREKSQELQKQIETLDKRIEKRSETIKEQARDTQVKQSS GSNVIDVVLNAESFTDAVSRVQAMTTIVKANNDLVEQQ KADKAEVEQKQAENQKQQEQITANQATLESQKGDLITK QADLNVQTTTLATQQATAESEKASLKEKQDAAVKEQQR VQEEARKAAEAQEAAQKAEADRKAKADSDAKAEADRK AQEEAATSTTTTESSTAESAATVESSSTEQQTQSSATESSS TASTSEDNFQGGGATPTTPSDTGNSSSSDQGSTSSSTNNQ TPSTPAPTPTPTPAPAPSGNTGGVVAEAMKYIGTPYVWG GKTPGGFDCSGFTSYVYRQATGREIGGWTVPQESAGTRI SVDQAQAGDLYFWGSPGGSYHVAIAMGGGQYIHAPQPG ETVTVSSVSYYAPSFAVRM (SEQ ID NO: 15) |

FIG. 2 (continued)

| Enterococcus avium (Eav) | WP_049219848.1 | MKKSLLSALMVCSVTLSALAAPAAASADEFDSKIADQD AKISSLQNQQTDAQSQISALEGEVASINDKAQGLLNEQES LRQKSQELQKQIETLDKRIEKRSEAIKEQARDTQVKQSSG TNVIDVVLNAESFTDAVSRVQAMTTIVKANNDLVEQQK ADKAEVEQKQAENKKQQEQIAANQATLESQKGDLIAKQ ADLNVQTTTLAAEQATAESDKASLKEKQEAAIKEQQRV QEEARKAAEAQEAAKKADAEAKEKADADAKAEADRK AQEEAAASTTTTESSSSTVESSSTEQTQSSTVDSSATESSN EDNFQGGGATPTTPSESGTGNTNSNNQGSTSSTTNNQTP STPAPTPTPTPAPSGNGSGVVAEAMKYIGTPYVWGGKTP AGFDCSGFTSYVFRQATGREIGGWTVPQESAGTRISVGE AQAGDLYFWGSPGGTYHVAIAMGGGQYIHAPQPGETVT VSSVSYYAPSFAVRM (SEQ ID NO: 16) |
|---|---|---|
| Enterococcus casseliflavus (Ecs) | WP_060793036.1 | MKKKIFATVCMCGIVLSSFGGPVTVFATNHDQLIEQKNN EIDQLRQQRQSVQGEIDSLNQEAAIILAQQSDLLQAIEGL DQEISQLEERIAKRSENIEKQARETQVNGKGDNFLTAVLE ADSVSDLVGRVHAMTTIIRANNEVIEQQKADQQAVEQK RAESQEKVAELQAAQSHLEAQKGVLEASQAELNVLVSQ LAYEEATKEEKEQLRAEKEAYEAEQARIREEAARVAAL QAQAEQAAQQQAEQAAAEAAALNEAAVQAEGTEADAE AESPEPAEEPAAPAETQPEETQESEPVETPEAPEEAPVDTP EIQEPETPVTPPAPETPADSAPAVPAPTPAPTPVTPTPAPTP APSPAPIVTPPAPIVTPPAPSAPASTNGAAIVAEAYKHIGK PYVWGAKGPDSFDCSGFTRYVFLQVTGRDIGGWTVPQE TAGTVISVSQAQPGDLLFWGSSGSTYHVAIALGGGQYIH APRPGQNVSVGSTAHFTPSFAVRM (SEQ ID NO: 17) |
| Enterococcus gallinarum (Egl) | WP_061054362.1 | MKKKIFATVCMCGIVLSSFGGPVTVFATNHDQLIEQKNN EIDQLRQQRQSVQGEIDGLSAEIDSLNQEAAIILAQQSDLL QAIEGLDQEISQLEERIAKRSENIEKQARETQVNGKGDHF LTAVLEANSVSDLVGRVHAMTTIIRANNEVIEQQKADQQ AVEQKRAESQEKVAELQAAQSHLEAQKGVLEASQAELN VLVSNLAYEEATKEEEKEQLRAEKEAYEAEQARIREEAA RVAALQAQAEQAAQQQAEQAAAEEAALNEAAVQVEST EPDVETESPAPVEEPEAPAETQPEETQESEPVETPEVPEET PVDTPEIHEPETPVTPATPETPADSAPAVPAPTPAPTPVTP TPAPTPAPSPAPIVTPPAPSAPASTNGAAIVAEAYKHIGKP YVWGAKGPDSFDCSGFTRYVFLQVTGRDIGGWTVPQET AGTVISVSQAQPGDLLFWGSSGSTYHVAIALGGGQYIHA PRPGQNVSVGSTAHFTPSFAVRM (SEQ ID NO: 18) |

FIG. 2 (continued)

| Species | Percent ID | Sequence |
|---|---|---|
| *Efm* | --- | GTPYVWGGKDPSGFDCSGFTRYVYLQVTGRDIGGWTVPQESAGTKISVSQAKAGDLLFWGSPGGTYHVAIALGGGQYIHAPQPGESVKVGSV (SEQ ID NO: 19) |
| *Evl* | 97.8 | GTPYVWGGKDPSGFDCSGFTRYVYLQVTGRDIGGWTVPQESAGAKISVSQAKAGDLLFWGSPGGTYHVAIALGGGQYIHAPQPGENVKVGSV (SEQ ID NO: 20) |
| *Ehr* | 96.4 | GTPYVWGGKDPSGFDCSGFTRYVYLQVTGRDIGGWTVPQESAGTKISVSQAKAGDLLFWGSAGGTYHVAISLGGGQYIHAPQPGENVKVGSV (SEQ ID NO: 21) |
| *Edr* | 94.6 | GVPYVWGGKDPSGFDCSGFTSYVYKQVTGRDIGGWTVPQENAGAKISVSQAKAGDLLFWGSPGGTYHVAIALGGGQYIHAPQPGESVKVGSV (SEQ ID NO: 22) |
| *Ert* | 94.6 | GVPYVWGGKDPSGFDCSGFTRYVYLQATGRDIGGWTVPQESAGTRISVSQAKAGDLLFWGSPGGSYHVAISLGGGQYIHAPQPGESVKVGSV (SEQ ID NO: 23) |
| *Emn* | 93.5 | GTPYVWGGKDPSGFDCSGFTRYVYLQVTGRDIGGWTVPQESAGARISVSQAKAGDLLFWGAAGGTYHVAISLGGGQYIHAPQPGESVKIGSV (SEQ ID NO: 24) |
| *Ehm* | 87.0 | GTPYVWGGKTPSGFDCSGFTAYVYRQATGREIGGWTVPQESAGTRISVSEAQAGDLYFWGSPGGSYHVAIAMGGGQYIHAPQPGESVKVGST (SEQ ID NO: 25) |
| *Eph* | 85.9 | GTPYVWGGKDPSGFDCSGFTSYVYRQATGREIGGWTVPQESAGAKIGINEAQAGDLLFWGSPGGTHHVAIALGGGQYIHAPQPGESVKIGSY (SEQ ID NO: 26) |
| *Ecb* | 83.7 | GKPYVWGAKGPDTFDCSGFTRYVYLQVTGRDIGGWTVPQESAGTVIPVSQAQPGDLYFWGSRGSTSHVAIAIGGGQYIHAPQPGETVKVGSV (SEQ ID NO: 27) |
| *Edv* | 83.7 | GTPYVWGGKTPAGFDCSGFTSYVFRQATGREIGGWTVPQESAGTRISVSQAQAGDLYFWGSPGGSYHVAIAMGGGQYIHAPQPGQSVTVSSV (SEQ ID NO: 28) |
| *Eml* | 83.7 | GTPYVWGGKTPGGFDCSGFTSYVYRQATGREIGGWTVPQESAGTRISVDQAQAGDLYFWGSPGGSYHVAIAMGGGQYIHAPQPGETVTVSSV (SEQ ID NO: 29) |
| *Erf* | 83.7 | GTPYVWGGKTPAGFDCSGFTSYVYRQATGREIGGWTVPQESAGTRISVDQAQAGDLYFWGSPGGSYHVAIAMGGGQYIHAPQPGETVTVSSV (SEQ ID NO: 30) |
| *Esc* | 83.7 | GVPYVWGGKDPSGFDCSGFTSYVYRKATGREIGGWTVPQESAGSVISVSEAKAGDLLFWGSQGSTYHVAIALGGGQYIHAPAPGQSVTVASV (SEQ ID NO: 31) |
| *Eav* | 82.6 | GTPYVWGGKTPAGFDCSGFTSYVFRQATGREIGGWTVPQESAGTRISVGEAQAGDLYFWGSPGGTYHVAIAMGGGQYIHAPQPGETVTVSSV (SEQ ID NO: 32) |
| *Ecc* | 82.6 | GKPYVWGAKGPNTFDCSGFTRYVYLQVTGRDIGGWTVPQEGAGAIIPVSQAQPGDLYFWGSRGSSYHVAIALGGGSYIHAPQPGESVKVGSV (SEQ ID NO: 33) |
| *Egv* | 82.6 | GTPYVWGGKTPAGFDCSGFTSYVFRQATGREIGGWTVPQESAGTRISVGEAQAGDLYFWGSPGGTYHVAIAMGGGQYIHAPQPGETVTVSSV (SEQ ID NO: 34) |
| *Ecs* | 81.5 | GKPYVWGAKGPDSFDCSGFTRYVFLQVTGRDIGGWTVPQETAGTVISVSQAQPGDLLFWGSSGSTYHVAIALGGGQYIHAPRPGQNVSVGST (SEQ ID NO: 35) |
| *Egl* | 81.5 | GKPYVWGAKGPDSFDCSGFTRYVFLQVTGRDIGGWTVPQETAGTVISVSQAQPGDLLFWGSSGSTYHVAIALGGGQYIHAPRPGQNVSVGST (SEQ ID NO: 36) |

FIG. 3

FIG. 8A SagA expression in *Enterococci*
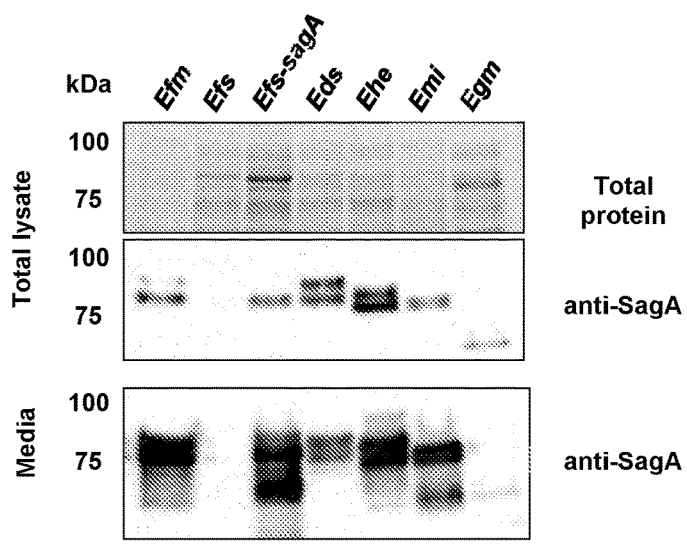
FIG. 8B *Enterococci* colonization
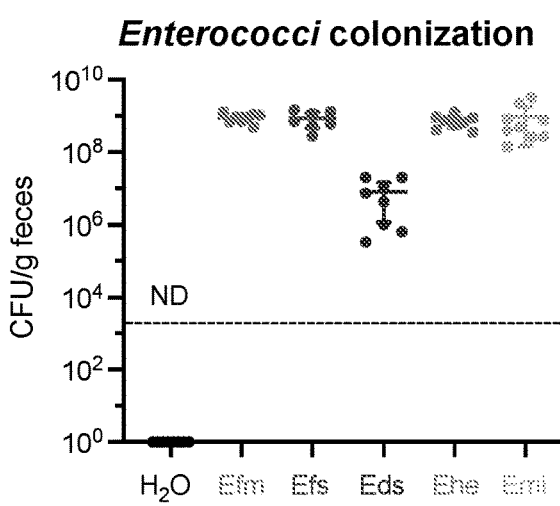
FIG. 8C αPD-L1 activity on B16/F10 melanoma
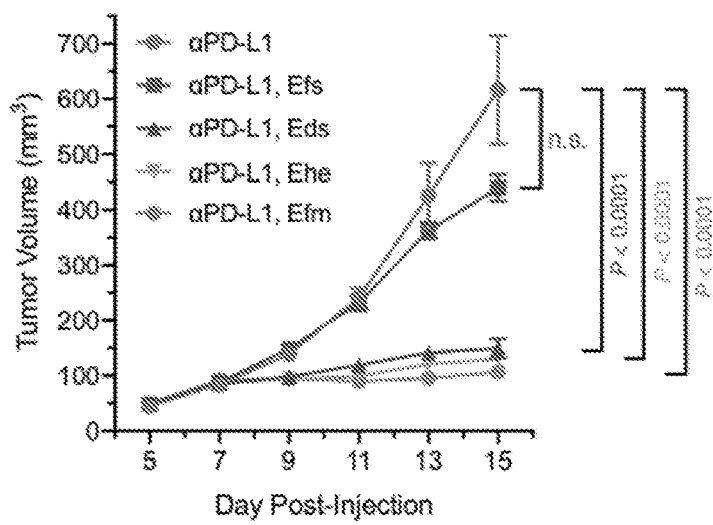

**L. lactis SagA Efficacy in an acute model of *C. difficile* infection**

SEQUENCE LISTING

```
<160> NUMBER OF SEQ ID NOS: 36

<210> SEQ ID NO 1
<211> LENGTH: 530
<212> TYPE: PRT
<213> ORGANISM: Enterococcus faecium

<400> SEQUENCE: 1

Met Lys Lys Ser Leu Ile Ser Ala Val Met Val Cys Ser Met Thr Leu
1               5                   10                  15

Thr Ala Val Ala Ser Pro Ile Ala Ala Ala Ala Asp Asp Phe Asp Ser
            20                  25                  30

Gln Ile Gln Gln Gln Asp Gln Lys Ile Ala Asp Leu Lys Asn Gln Gln
        35                  40                  45

Ala Asp Ala Gln Ser Gln Ile Asp Ala Leu Glu Ser Gln Val Ser Glu
    50                  55                  60

Ile Asn Thr Gln Ala Gln Asp Leu Leu Ala Lys Gln Asp Thr Leu Arg
65                  70                  75                  80

Gln Glu Ser Ala Gln Leu Val Lys Asp Ile Ala Asp Leu Gln Glu Arg
                85                  90                  95

Ile Glu Lys Arg Glu Asp Thr Ile Gln Lys Gln Ala Arg Glu Ala Gln
            100                 105                 110

Val Ser Asn Thr Ser Ser Asn Tyr Ile Asp Ala Val Leu Asn Ala Asp
        115                 120                 125

Ser Leu Ala Asp Ala Ile Gly Arg Val Gln Ala Met Thr Thr Met Val
    130                 135                 140

Lys Ala Asn Asn Asp Leu Met Glu Gln Gln Lys Gln Asp Lys Lys Ala
145                 150                 155                 160
```

Val Glu Asp Lys Lys Ala Glu Asn Asp Ala Lys Leu Lys Glu Leu Ala
            165                 170                 175

Glu Asn Gln Ala Ala Leu Glu Ser Gln Lys Gly Asp Leu Leu Ser Lys
        180                 185                 190

Gln Ala Asp Leu Asn Val Leu Lys Thr Ser Leu Ala Ala Glu Gln Ala
        195                 200                 205

Thr Ala Glu Asp Lys Lys Ala Asp Leu Asn Arg Gln Lys Ala Glu Ala
    210                 215                 220

Glu Ala Glu Gln Ala Arg Ile Arg Glu Gln Gln Arg Leu Ala Glu Gln
225                 230                 235                 240

Ala Arg Gln Gln Ala Ala Gln Glu Lys Ala Lys Glu Ala Arg Glu
                245                 250                 255

Gln Ala Glu Ala Glu Ala Gln Ala Thr Gln Ala Ser Ser Thr Ala Gln
                260                 265                 270

Ser Ser Ala Ser Glu Glu Ser Ser Ala Ala Gln Ser Ser Thr Thr Glu
        275                 280                 285

Glu Ser Ser Ser Ala Ala Gln Ser Ser Thr Thr Glu Glu Ser Thr Thr
    290                 295                 300

Ala Pro Glu Ser Ser Thr Thr Glu Glu Ser Thr Thr Ala Pro Glu Ser
305                 310                 315                 320

Ser Thr Thr Glu Glu Ser Thr Val Pro Glu Ser Ser Thr Thr Glu
                325                 330                 335

Glu Ser Thr Thr Val Pro Glu Ser Ser Thr Glu Glu Ser Thr Thr
                340                 345                 350

Val Pro Glu Ser Ser Thr Glu Ser Thr Thr Val Pro Glu Thr
        355                 360                 365

Ser Thr Glu Glu Ser Thr Thr Pro Ala Pro Thr Thr Pro Ser Thr Asp
    370                 375                 380

Gln Ser Val Asp Pro Gly Asn Ser Thr Gly Ser Asn Ala Thr Asn Asn
385                 390                 395                 400

Thr Thr Asn Thr Thr Pro Thr Pro Thr Pro Ser Gly Ser Val Asn Gly
                405                 410                 415

Ala Ala Ile Val Ala Glu Ala Tyr Lys Tyr Ile Gly Thr Pro Tyr Val
                420                 425                 430

Trp Gly Gly Lys Asp Pro Ser Gly Phe Asp Cys Ser Gly Phe Thr Arg
        435                 440                 445

Tyr Val Tyr Leu Gln Val Thr Gly Arg Asp Ile Gly Gly Trp Thr Val
    450                 455                 460

Pro Gln Glu Ser Ala Gly Thr Lys Ile Ser Val Ser Gln Ala Lys Ala
465                 470                 475                 480

Gly Asp Leu Leu Phe Trp Gly Ser Pro Gly Gly Thr Tyr His Val Ala
                485                 490                 495

Ile Ala Leu Gly Gly Gly Gln Tyr Ile His Ala Pro Gln Pro Gly Glu
                500                 505                 510

Ser Val Lys Val Gly Ser Val Gln Trp Phe Ala Pro Asp Phe Ala Val
        515                 520                 525

Ser Met
    530

<210> SEQ ID NO 2
<211> LENGTH: 518
<212> TYPE: PRT
<213> ORGANISM: Enterococcus durans

<400> SEQUENCE: 2

```
Met Lys Lys Ser Leu Ile Ser Ala Val Met Leu Ser Ser Ile Ala Leu
1               5                   10                  15

Thr Ala Val Gly Ser Pro Ile Ala Ala Ala Asp Asp Phe Asp Ser
            20                  25                  30

Gln Ile Gln Gln Gln Asp Gln Lys Ile Ala Asp Leu Gln Asn Gln Gln
                35                  40                  45

Ala Ser Ala Gln Ser Gln Ile Glu Ala Leu Glu Gly Gln Val Ser Ser
        50                  55                  60

Ile Asn Ala Lys Ala Gln Asp Leu Leu Thr Lys Gln Asp Thr Leu Arg
65                  70                  75                  80

Lys Glu Ser Ser Gln Leu Glu Lys Glu Ile Ala Asp Leu Gln Glu Arg
                85                  90                  95

Ile Glu Lys Arg Glu Ala Thr Ile Gln Lys Gln Ala Arg Glu Thr Gln
                100                 105                 110

Val Lys Asn Thr Ser Ser Asn Tyr Ile Asp Ala Val Leu Asn Ala Asp
            115                 120                 125

Ser Leu Ala Asp Ala Val Gly Arg Ile Gln Ala Met Thr Ser Ile Val
        130                 135                 140

Lys Ala Asn Gln Asp Leu Val Asp Gln Gln Lys Gln Asp Lys Gln Ala
145                 150                 155                 160

Val Glu Asp Lys Lys Ala Glu Asn Glu Ala Lys Gln Lys Glu Leu Ser
                165                 170                 175

Ala Asn Gln Ala Thr Leu Glu Ser Gln Lys Gly Asp Leu Leu Ala Lys
                180                 185                 190

Gln Ala Asp Leu Asn Val Leu Lys Thr Ser Leu Ala Ala Glu Gln Ala
        195                 200                 205

Thr Ala Glu Asp Lys Lys Ala Asp Leu Asn Arg Lys Lys Ala Glu Ala
210                 215                 220

Glu Ala Glu Gln Ala Arg Ile Arg Glu Gln Ala Arg Leu Ala Glu Gln
225                 230                 235                 240

Ala Arg Gln Gln Ala Ala Gln Glu Lys Ala Glu Lys Glu Ala Arg Glu
                245                 250                 255

Gln Ala Ala Ala Gln Ala Ala Gln Ser Gln Ala Ala Gln Ser Gln Ala
                260                 265                 270

Ala Ser Ser Ala Ser Thr Thr Glu Asn Ser Ser Thr Val Gln Ser Ser
            275                 280                 285

Thr Thr Glu Asn Ser Ser Ser Ser Ala Gln Ser Ser Ser Ser Ser Ser
        290                 295                 300

Ser Ala Val Val Thr Pro Gly Ser Ser Ser Thr Thr Glu Glu Ser Thr
305                 310                 315                 320

Val Pro Glu Ser Ser Thr Ser Thr Thr Glu Asn Ser Ser Thr Glu Ser
                325                 330                 335

Ser Thr Asp Ser Ser Val Thr Glu Ser Thr Val Pro Glu Ser
        340                 345                 350

Ser Thr Gln Glu Thr Thr Pro Ala Thr Pro Thr Thr Pro Ser Thr Pro
        355                 360                 365

Ala Thr Ser Asn Asn Gly Ser Thr Gly Asn Gly Thr Pro Asn Asn
        370                 375                 380

Thr Gly Thr Val Val Thr Pro Pro Thr Thr Pro Ser Thr Pro Ser Gly
385                 390                 395                 400

Ser Val Asn Gly Ser Ala Ile Val Ala Glu Ala Tyr Lys Tyr Ile Gly
                405                 410                 415
```

```
Val Pro Tyr Val Trp Gly Gly Lys Asp Pro Ser Gly Phe Asp Cys Ser
            420                 425                 430

Gly Phe Thr Ser Tyr Val Tyr Lys Gln Val Thr Gly Arg Asp Ile Gly
            435                 440                 445

Gly Trp Thr Val Pro Gln Glu Asn Ala Gly Ala Lys Ile Ser Val Ser
        450                 455                 460

Gln Ala Lys Ala Gly Asp Leu Leu Phe Trp Gly Ser Pro Gly Gly Thr
465                 470                 475                 480

Tyr His Val Ala Ile Ala Leu Gly Gly Gln Tyr Ile His Ala Pro
                485                 490                 495

Gln Pro Gly Glu Ser Val Lys Val Gly Ser Val Gln Trp Phe Ala Pro
            500                 505                 510

Asp Phe Ala Val Ser Met
            515
```

<210> SEQ ID NO 3
<211> LENGTH: 516
<212> TYPE: PRT
<213> ORGANISM: Enterococcus hirae

<400> SEQUENCE: 3

```
Met Lys Lys Ser Leu Leu Ser Ala Val Met Leu Ser Ser Ile Ala Leu
1               5                   10                  15

Thr Ala Val Gly Ser Pro Ile Ala Ala Ala Asp Asp Phe Asp Ser
            20                  25                  30

Gln Ile Gln Gln Gln Asp Lys Lys Ile Ala Asp Leu Gln Asn Gln Gln
        35                  40                  45

Ala Ser Ala Gln Ser Gln Ile Glu Ala Leu Glu Gly Gln Val Ser Ala
50                  55                  60

Ile Asn Thr Lys Ala Gln Asp Leu Leu Thr Lys Gln Asp Thr Leu Arg
65                  70                  75                  80

Lys Glu Ser Ala Gln Leu Lys Gln Glu Ile Lys Asp Leu Gln Glu Arg
                85                  90                  95

Ile Glu Lys Arg Glu Ala Thr Ile Gln Lys Gln Ala Arg Glu Thr Gln
            100                 105                 110

Val Lys Asn Thr Ser Ser Asn Tyr Ile Asp Ala Val Leu Asn Ala Asp
        115                 120                 125

Ser Leu Ala Asp Ala Val Gly Arg Ile Gln Ala Met Ser Thr Ile Val
        130                 135                 140

Lys Ala Asn Gln Asp Leu Val Gln Gln Lys Glu Asp Lys Gln Ala
145                 150                 155                 160

Val Glu Ala Lys Lys Ala Glu Asn Glu Ala Lys Gln Lys Glu Leu Ala
                165                 170                 175

Asp Asn Gln Ala Ala Leu Glu Ser Gln Lys Gly Asp Leu Leu Ala Lys
            180                 185                 190

Gln Ala Asp Leu Asn Val Leu Lys Thr Ser Leu Ala Ala Glu Gln Ala
        195                 200                 205

Thr Ala Glu Asp Lys Lys Ala Asp Leu Asn Arg Lys Lys Ala Glu Ala
    210                 215                 220

Glu Ala Glu Gln Ala Arg Ile Arg Glu Gln Arg Leu Ala Glu Gln
225                 230                 235                 240

Ala Arg Gln Gln Ala Ala Gln Glu Lys Ala Glu Lys Glu Ala Arg Glu
                245                 250                 255

Gln Ala Ala Ala Gln Ala Ala Gln Thr Gln Ala Leu Ser Ser Ala Ser
```

```
                    260                 265                 270
Thr Thr Thr Glu Ser Ser Ala Ala Gln Ser Ser Glu Glu Ser
            275                 280                 285
Lys Ala Pro Glu Ser Ser Thr Glu Glu Ser Thr Ser Thr Glu Ser
        290                 295                 300
Ser Thr Thr Thr Glu Asn Ser Ser Thr Gly Ser Ser Ser Thr Glu Ser
305                 310                 315                 320
Ser Ser Thr Glu Glu Ser Thr Val Pro Glu Ser Ser Thr Gln Glu Ser
                325                 330                 335
Thr Pro Ala Asn Thr Glu Ser Ser Ser Ser Ser Asn Thr Asn Val
            340                 345                 350
Asn Asn Asn Thr Asn Asn Ser Thr Asn Asn Ser Thr Asn Asn Ser Thr
        355                 360                 365
Thr Asn Asn Asn Asn Asn Asn Thr Val Thr Pro Ala Pro Thr Pro
    370                 375                 380
Thr Pro Thr Pro Ala Pro Ala Pro Ala Pro Asn Pro Ser Gly Ser Val
385                 390                 395                 400
Asn Gly Ala Ala Ile Val Ala Glu Ala Tyr Lys Tyr Ile Gly Thr Pro
                405                 410                 415
Tyr Val Trp Gly Gly Lys Asp Pro Ser Gly Phe Asp Cys Ser Gly Phe
                420                 425                 430
Thr Arg Tyr Val Tyr Leu Gln Val Thr Gly Arg Asp Ile Gly Gly Trp
            435                 440                 445
Thr Val Pro Gln Glu Ser Ala Gly Thr Lys Ile Ser Val Ser Gln Ala
        450                 455                 460
Lys Ala Gly Asp Leu Leu Phe Trp Gly Ser Ala Gly Gly Thr Tyr His
465                 470                 475                 480
Val Ala Ile Ser Leu Gly Gly Gly Gln Tyr Ile His Ala Pro Gln Pro
                485                 490                 495
Gly Glu Asn Val Lys Val Gly Ser Val Gln Trp Tyr Thr Pro Asp Phe
            500                 505                 510
Ala Val Ser Met
        515

<210> SEQ ID NO 4
<211> LENGTH: 500
<212> TYPE: PRT
<213> ORGANISM: Enterococcus mundtii

<400> SEQUENCE: 4

Met Lys Lys Ser Leu Ile Ser Ala Val Met Val Ser Ser Met Ala Leu
1               5                   10                  15
Thr Ala Val Ala Ser Pro Ile Ala Ala Ala Glu Asp Phe Asp Ser
            20                  25                  30
Gln Ile Gln Gln Gln Asp Gln Lys Ile Ala Glu Leu Gln Asn Gln Gln
        35                  40                  45
Ala Ser Ala Gln Ser Gln Ile Glu Ala Leu Glu Gly Gln Val Ala Asp
    50                  55                  60
Ile Asn Thr Lys Ala Glu Thr Leu Leu Ala Asn Gln Ala Thr Leu Arg
65                  70                  75                  80
Gln Glu Ser Ser Gln Leu Thr Gln Glu Ile Ala Asp Leu Gln Glu Arg
                85                  90                  95
Ile Glu Lys Arg Glu Ala Thr Ile Gln Glu Gln Ala Arg Glu Thr Gln
            100                 105                 110
```

```
Val Lys Gly Thr Ser Ser Asn Tyr Ile Asp Ala Val Leu Asn Ala Glu
            115                 120                 125
Ser Phe Ser Asp Ala Ile Gly Arg Val Gln Ala Met Ser Ser Ile Val
        130                 135                 140
Arg Ala Asn Gln Asp Leu Val Lys Gln Lys Glu Asp Lys Gln Ala
145                 150                 155                 160
Val Glu Asp Lys Lys Ala Glu Asn Glu Ala Lys Leu Gln Glu Leu Ala
                165                 170                 175
Glu Asn Gln Ala Ala Leu Glu Ser Gln Lys Gly Asp Leu Leu Ser Lys
            180                 185                 190
Gln Ala Asp Leu Asn Val Leu Lys Thr Thr Leu Ala Ala Glu Gln Ala
        195                 200                 205
Thr Ala Glu Asp Lys Lys Glu Asp Leu Asn Arg Gln Lys Ala Glu Ala
    210                 215                 220
Glu Ala Glu Gln Ala Arg Ile Arg Glu Gln Ala Arg Leu Ala Glu Gln
225                 230                 235                 240
Ala Arg Gln Gln Ala Ala Gln Glu Gln Ala Glu Arg Glu Ala Arg Glu
                245                 250                 255
Gln Ala Ala Val Ala Ala Ala Ala Gln Glu Gln Glu Gln Ala Ser
            260                 265                 270
Ser Ser Ser Val Gln Glu Ser Thr Glu Val Ser Glu Ser Ala Thr Ser
        275                 280                 285
Glu Ser Ser Ser Ser Ala Glu Ser Ser Thr Glu Gln Ser Ser Val Pro
    290                 295                 300
Glu Ser Ser Thr Ser Thr Glu Asp Ser Thr Thr Glu Ser Ser Val Pro
305                 310                 315                 320
Glu Ser Ser Thr Glu Glu Ser Thr Thr Thr Pro Ser Val Pro Glu Thr
                325                 330                 335
Thr Thr Pro Ser Thr Pro Glu Pro Ser Thr Pro Ala Pro Ser Thr Pro
            340                 345                 350
Glu Pro Ser Thr Pro Ala Pro Ser Thr Pro Ala Pro Ser Thr Pro Glu
        355                 360                 365
Pro Ser Thr Pro Ala Pro Ser Ile Pro Ala Pro Thr Ala Pro Ser Thr
    370                 375                 380
Asn Gly Ala Ala Ile Val Ala Glu Ala Met Lys Tyr Ile Gly Thr Pro
385                 390                 395                 400
Tyr Val Trp Gly Gly Lys Asp Pro Ser Gly Phe Asp Cys Ser Gly Phe
                405                 410                 415
Thr Arg Tyr Val Tyr Leu Gln Val Thr Gly Arg Asp Ile Gly Gly Trp
            420                 425                 430
Thr Val Pro Gln Glu Ser Ala Gly Ala Arg Ile Ser Val Ser Gln Ala
        435                 440                 445
Lys Ala Gly Asp Leu Leu Phe Trp Gly Ala Gly Gly Thr Tyr His
    450                 455                 460
Val Ala Ile Ser Leu Gly Gly Gln Tyr Ile His Ala Pro Gln Pro
465                 470                 475                 480
Gly Glu Ser Val Lys Ile Gly Ser Val Gln Trp Tyr Ala Pro Asp Phe
                485                 490                 495
Ala Val Ser Met
            500

<210> SEQ ID NO 5
<211> LENGTH: 484
<212> TYPE: PRT
```

<213> ORGANISM: Enterococcus raffinosus

<400> SEQUENCE: 5

Met Lys Lys Ser Leu Leu Ser Ala Leu Met Val Cys Ser Val Thr Leu
1               5                   10                  15

Ser Ala Leu Ala Ala Pro Ala Ala Ser Ala Asp Glu Phe Asp Ser
            20                  25                  30

Lys Ile Ala Asp Gln Asp Ala Lys Ile Ser Ser Leu Gln Asn Gln Gln
        35                  40                  45

Thr Asp Ala Gln Ser Gln Ile Ser Ala Leu Glu Gly Glu Val Ala Ser
    50                  55                  60

Ile Asn Glu Lys Ala Gln Gly Leu Leu Asn Glu Gln Ala Ser Leu Arg
65                  70                  75                  80

Gln Glu Ser Gln Asp Leu Gln Lys Gln Ile Glu Thr Leu Gln Lys Arg
                85                  90                  95

Ile Glu Lys Arg Ser Glu Ala Ile Lys Glu Gln Ala Arg Asp Thr Gln
            100                 105                 110

Val Lys Gln Ser Ser Gly Thr Asn Val Ile Asp Val Leu Asn Ala
        115                 120                 125

Glu Ser Phe Thr Asp Ala Val Ser Arg Val Gln Ala Met Thr Thr Ile
130                 135                 140

Val Lys Ala Asn Asn Asp Leu Val Glu Gln Gln Lys Ala Asp Lys Ala
145                 150                 155                 160

Glu Val Glu Gln Lys Gln Ala Glu Asn Lys Lys Gln Glu Gln Ile
            165                 170                 175

Ala Ala Asn Gln Ala Thr Leu Glu Ser Gln Lys Gly Glu Leu Ile Thr
        180                 185                 190

Lys Gln Ala Asp Leu Asn Val Gln Thr Thr Thr Leu Ala Ala Glu Gln
    195                 200                 205

Ala Thr Ala Glu Gly Glu Lys Ala Ser Leu Lys Glu Lys Gln Glu Ala
    210                 215                 220

Ala Ile Lys Glu Gln Glu Arg Val Gln Glu Glu Ala Arg Lys Ala Ala
225                 230                 235                 240

Glu Ala Gln Glu Ala Ala Lys Lys Ala Asp Ala Asp Ala Lys Ala Lys
            245                 250                 255

Ala Asp Ala Asp Ala Lys Ala Glu Ala Asp Arg Lys Ala Gln Glu Glu
        260                 265                 270

Ala Ala Ala Ser Thr Thr Thr Glu Ser Ser Thr Val Glu Ser Ser
    275                 280                 285

Ser Thr Val Glu Ser Ser Thr Thr Glu Gln Gln Thr Gln Ser Ser Ala
    290                 295                 300

Thr Glu Ser Ser Ser Thr Ala Ser Ser Ser Glu Asp Asn Phe Gln Gly
305                 310                 315                 320

Gly Gly Ala Thr Pro Thr Pro Ser Thr Thr Glu Asp Ser Gly Ser Ser
            325                 330                 335

Asn Gln Gly Ser Thr Ser Ser Thr Asn Asn Asn Gln Thr Pro Ser
        340                 345                 350

Thr Pro Thr Pro Ala Pro Thr Pro Thr Pro Ala Pro Ala Pro Ser Gly
    355                 360                 365

Asn Thr Gly Gly Val Val Ala Glu Ala Met Lys Tyr Ile Gly Thr Pro
    370                 375                 380

Tyr Val Trp Gly Gly Lys Thr Pro Ala Gly Phe Asp Cys Ser Gly Phe
385                 390                 395                 400

```
Thr Ser Tyr Val Tyr Arg Gln Ala Thr Gly Arg Glu Ile Gly Gly Trp
            405                 410                 415

Thr Val Pro Gln Glu Ser Ala Gly Thr Arg Ile Ser Val Asp Gln Ala
            420                 425                 430

Gln Ala Gly Asp Leu Tyr Phe Trp Gly Ser Pro Gly Gly Ser Tyr His
            435                 440                 445

Val Ala Ile Ala Met Gly Gly Gln Tyr Ile His Ala Pro Gln Pro
450                 455                 460

Gly Glu Thr Val Thr Val Ser Ser Val Ser Tyr Tyr Ala Pro Ser Phe
465                 470                 475                 480

Ala Val Arg Met

<210> SEQ ID NO 6
<211> LENGTH: 484
<212> TYPE: PRT
<213> ORGANISM: Enterococcus gilvus

<400> SEQUENCE: 6

Met Lys Lys Ser Leu Leu Ser Ala Leu Met Val Cys Ser Val Thr Leu
1               5                   10                  15

Ser Ala Leu Ala Ala Pro Ala Ala Ser Ala Asp Glu Phe Asp Ser
            20                  25                  30

Lys Ile Ala Asp Gln Asp Ala Lys Ile Ser Ser Leu Gln Asn Gln Gln
            35                  40                  45

Thr Asp Ala Gln Ser Gln Ile Ser Ala Leu Glu Gly Glu Val Ala Ser
        50                  55                  60

Ile Asn Asp Lys Ala Gln Gly Leu Leu Asn Glu Gln Ala Ser Leu Lys
65                  70                  75                  80

Gln Lys Ser Gln Glu Leu Gln Lys Gln Ile Glu Thr Leu Asp Lys Arg
            85                  90                  95

Ile Glu Lys Arg Ser Glu Ala Ile Lys Glu Gln Ala Arg Ser Ala Gln
            100                 105                 110

Val Lys Gln Ser Ser Gly Ser Asn Val Val Asp Val Val Leu Asn Ala
            115                 120                 125

Glu Ser Phe Thr Asp Val Val Ser Arg Val Gln Ala Met Ala Thr Ile
        130                 135                 140

Ala Lys Ala Asn Asn Asp Leu Val Glu Gln Gln Lys Ala Asp Lys Ala
145                 150                 155                 160

Glu Val Glu Gln Lys Gln Ser Glu Asn Gln Lys Leu Glu Gln Ile
            165                 170                 175

Ala Ala Asn Gln Ala Thr Leu Glu Ser Gln Lys Gly Asp Leu Ile Thr
            180                 185                 190

Lys Gln Ala Asp Leu Asn Val Gln Thr Thr Leu Ala Ala Asp Gln
        195                 200                 205

Ala Thr Ala Glu Gly Glu Lys Ala Ser Leu Lys Glu Lys Gln Asp Ala
        210                 215                 220

Ala Ile Lys Glu Gln Gln Arg Val Gln Glu Glu Ala Arg Lys Ala Ala
225                 230                 235                 240

Glu Ala Gln Glu Ala Ala Lys Lys Ala Glu Thr Asp Ala Lys Ala Lys
            245                 250                 255

Ala Asp Ala Asp Ala Lys Ala Glu Ala Asp Arg Lys Ala Gln Glu Glu
            260                 265                 270

Ala Ala Ala Ser Thr Thr Thr Thr Glu Ser Ser Thr Val Glu Ser Ser
        275                 280                 285
```

```
Thr Thr Val Glu Thr Ser Ser Thr Glu Gln Gln Thr Ser Thr Thr Glu
    290                 295                 300

Ser Ser Ser Ser Glu Ser Ser Glu Asp Asn Phe Gln Gly Gly Gly
305                 310                 315                 320

Ala Thr Pro Thr Asp Asn Gly Asn Ser Ser Ala Asn Asn Asn Gln Gly
                325                 330                 335

Ser Thr Ser Ser Ser Thr Asn Asp Gln Thr Pro Ala Pro Thr Pro Thr
            340                 345                 350

Pro Ala Pro Glu Val Pro Lys Pro Ser Thr Pro Thr Pro Pro Ala
        355                 360                 365

Thr Ser Gly Ser Val Val Ala Glu Ala Met Lys Tyr Ile Gly Thr Pro
370                 375                 380

Tyr Val Trp Gly Gly Lys Thr Pro Ala Gly Phe Asp Cys Ser Gly Phe
385                 390                 395                 400

Thr Ser Tyr Val Phe Arg Gln Ala Thr Gly Arg Glu Ile Gly Trp
                405                 410                 415

Thr Val Pro Gln Glu Ser Ala Gly Thr Arg Ile Ser Val Gly Glu Ala
                420                 425                 430

Gln Ala Gly Asp Leu Tyr Phe Trp Gly Ser Pro Gly Gly Thr Tyr His
            435                 440                 445

Val Ala Ile Ala Met Gly Gly Gly Gln Tyr Ile His Ala Pro Gln Pro
450                 455                 460

Gly Glu Thr Val Thr Val Ser Ser Val Ser Tyr Tyr Ala Pro Ser Phe
465                 470                 475                 480

Ala Val Arg Met

<210> SEQ ID NO 7
<211> LENGTH: 505
<212> TYPE: PRT
<213> ORGANISM: Enterococcus villorum

<400> SEQUENCE: 7

Met Lys Lys Ser Leu Leu Ser Ala Val Met Leu Ser Ser Ile Ala Leu
1               5                   10                  15

Thr Ala Val Gly Ser Pro Ile Ala Ala Ala Asp Asp Phe Asp Ser
            20                  25                  30

Gln Ile Gln Gln Gln Asp Lys Lys Ile Ala Asp Leu Gln Asn Gln Gln
        35                  40                  45

Leu Ser Ala Gln Ser Gln Ile Glu Ala Leu Glu Gly Gln Val Ser Ala
50                  55                  60

Ile Asn Thr Lys Ala Gln Asp Leu Leu Ala Lys Gln Asp Thr Leu Arg
65                  70                  75                  80

Lys Glu Ser Thr Gln Leu Lys Lys Glu Ile Ala Asp Leu Gln Glu Arg
                85                  90                  95

Ile Glu Lys Arg Glu Ala Thr Ile Gln Lys Gln Ala Arg Glu Thr Gln
            100                 105                 110

Val Lys Asn Thr Ser Ser Asn Tyr Ile Asp Ala Val Leu Asn Ala Asp
        115                 120                 125

Ser Leu Ala Asp Ala Val Gly Arg Ile Gln Ala Met Ser Ser Ile Val
130                 135                 140

Lys Ala Asn Gln Asp Leu Val Gln Gln Lys Glu Asp Lys Gln Ala
145                 150                 155                 160

Val Glu Ala Lys Lys Ala Glu Asn Glu Ala Lys Gln Lys Glu Leu Ala
                165                 170                 175
```

Glu Asn Gln Ala Ala Leu Glu Ser Gln Lys Gly Asp Leu Leu Ala Lys
            180                 185                 190

Gln Ala Asp Leu Asn Val Leu Lys Thr Ser Leu Ala Ala Glu Gln Ala
        195                 200                 205

Thr Ala Glu Asp Lys Lys Ala Asp Leu Asn Arg Lys Lys Ala Glu Ala
    210                 215                 220

Glu Ala Glu Gln Ala Arg Ile Arg Glu Gln Ala Arg Leu Ala Glu Gln
225                 230                 235                 240

Ala Arg Gln Gln Ala Gln Glu Lys Ala Lys Glu Ala Arg Glu
                245                 250                 255

Gln Ala Ala Ala Gln Ala Leu Ser Gln Ala Thr Ser Thr Thr Glu
            260                 265                 270

Ser Ser Ser Thr Val Ser Ser Thr Thr Glu Ser Ser Val Ala
        275                 280                 285

Gln Ser Ser Ser Glu Glu Ser Thr Thr Ser Glu Ser Ser Thr Thr Thr
    290                 295                 300

Thr Glu Glu Ser Thr Thr Ser Glu Ser Ser Thr Thr Thr Glu Glu
305                 310                 315                 320

Ser Thr Val Pro Glu Ser Ser Thr Thr Thr Glu Asn Ser Ser Thr Asp
                325                 330                 335

Ser Ser Thr Thr Glu Ser Ser Val Thr Glu Ser Ser Thr Val Pro Glu
            340                 345                 350

Ser Ser Thr Gln Asp Ser Thr Thr Ser Thr Asn Thr Ser Asn Ser Asn
        355                 360                 365

Asn Ser Asn Asn Ala Thr Thr Pro Thr Thr Pro Ser Thr Pro Ser Thr
370                 375                 380

Pro Ser Gly Ser Val Asn Gly Ala Ala Ile Val Ala Glu Ala Tyr Lys
385                 390                 395                 400

Tyr Ile Gly Thr Pro Tyr Val Trp Gly Gly Lys Asp Pro Ser Gly Phe
                405                 410                 415

Asp Cys Ser Gly Phe Thr Arg Tyr Val Tyr Leu Gln Val Thr Gly Arg
            420                 425                 430

Asp Ile Gly Gly Trp Thr Val Pro Gln Glu Ser Ala Gly Ala Lys Ile
        435                 440                 445

Ser Val Ser Gln Ala Lys Ala Gly Asp Leu Leu Phe Trp Gly Ser Pro
    450                 455                 460

Gly Gly Thr Tyr His Val Ala Ile Ala Leu Gly Gly Gln Tyr Ile
465                 470                 475                 480

His Ala Pro Gln Pro Gly Glu Asn Val Lys Val Gly Ser Val Gln Trp
                485                 490                 495

Tyr Ala Pro Asp Phe Ala Val Ser Met
            500                 505

<210> SEQ ID NO 8
<211> LENGTH: 509
<212> TYPE: PRT
<213> ORGANISM: Enterococcus ratti

<400> SEQUENCE: 8

Met Lys Lys Ser Leu Leu Ser Ala Val Met Leu Ser Ser Ile Ala Leu
1               5                   10                  15

Thr Ala Val Gly Ser Pro Ile Ala Ala Ala Glu Asp Phe Asp Ser
            20                  25                  30

Gln Ile Gln Gln Gln Asp Lys Lys Ile Ala Asp Leu Gln Asn Gln Gln
        35                  40                  45

-continued

```
Ser Ser Ala Gln Ala Gln Ile Glu Ala Leu Glu Asp Gln Val Ser Thr
 50                  55                  60

Ile Asn Ala Gln Ala Gln Asp Leu Leu Ala Lys Gln Ala Thr Leu Arg
 65                  70                  75                  80

Lys Glu Ser Ala Gln Leu Lys Gln Glu Ile Ala Asp Leu Gln Glu Arg
                 85                  90                  95

Ile Glu Lys Arg Glu Ala Thr Ile Gln Lys Gln Ala Arg Glu Thr Gln
                100                 105                 110

Val Lys Asn Thr Ser Ser Asn Tyr Ile Asp Ala Val Leu Asn Ala Asp
                115                 120                 125

Ser Phe Ala Asp Ala Ile Gly Arg Ile Gln Ala Met Ser Ser Ile Val
130                 135                 140

Lys Ala Asn Gln Glu Leu Val Gln Gln Lys Glu Asp Lys Gln Ala
145                 150                 155                 160

Val Glu Ala Lys Lys Asn Glu Asn Ala Lys Gln Lys Glu Leu Ala
                165                 170                 175

Lys Asn Gln Ala Val Leu Glu Ser Gln Lys Gly Asp Leu Leu Ala Lys
                180                 185                 190

Gln Ala Asp Leu Asn Val Leu Lys Thr Ser Leu Ala Ala Glu Gln Ala
                195                 200                 205

Thr Ala Glu Gly Lys Lys Ala Glu Leu Asn Arg Lys Lys Ala Glu Ala
210                 215                 220

Gln Ala Glu Gln Ala Arg Ile Arg Glu Gln Ala Arg Leu Ala Glu Gln
225                 230                 235                 240

Ala Arg Gln Gln Ala Arg Glu Lys Ala Lys Glu Ala Arg Glu
                245                 250                 255

Gln Ala Ala Ala Gln Thr Lys Ala Ser Thr Thr Glu Asp Ser Ser Val
                260                 265                 270

Ala Gln Ser Ser Ser Gln Glu Ser Ala Ala Ser Glu Ser Ser Thr Thr
                275                 280                 285

Ser Thr Glu Gly Ser Ser Thr Ala Asn Ser Ser Thr Thr Ala Glu Asn
290                 295                 300

Ser Ser Thr Gly Ser Ser Ser Glu Ser Ser Val Thr Asp Glu Ser
305                 310                 315                 320

Thr Ile Ser Asp Ser Ser Thr Ser Asp Ser Thr Pro Ala Thr Asp Ser
                325                 330                 335

Gly Ser Ser Asn Ser Ser Ser Asn Asn Ala Gly Asn Thr Ser Asp
                340                 345                 350

Ser Ser Ser Asp Ser Ser Asn Pro Thr Gly Asp Ser Ser Thr Ser Asn
                355                 360                 365

Asp Thr Asn Asn Thr Asn Asn Ser Asp Asn Ala Val Val Pro Thr Pro
370                 375                 380

Ala Pro Ser Gln Pro Ala Gly Ser Val Asn Gly Ser Ser Ile Val Ala
385                 390                 395                 400

Glu Ala Tyr Lys Tyr Ile Gly Val Pro Tyr Val Trp Gly Gly Lys Asp
                405                 410                 415

Pro Ser Gly Phe Asp Cys Ser Gly Phe Thr Arg Tyr Val Tyr Leu Gln
                420                 425                 430

Ala Thr Gly Arg Asp Ile Gly Gly Trp Thr Val Pro Gln Glu Ser Ala
                435                 440                 445

Gly Thr Arg Ile Ser Val Ser Gln Ala Lys Ala Gly Asp Leu Leu Phe
450                 455                 460
```

-continued

```
Trp Gly Ser Pro Gly Ser Tyr His Val Ala Ile Ser Leu Gly Gly
465                 470                 475                 480

Gly Gln Tyr Ile His Ala Pro Gln Pro Gly Glu Ser Val Lys Val Gly
            485                 490                 495

Ser Val Gln Trp Phe Ala Pro Asp Phe Ala Val Ser Met
            500                 505

<210> SEQ ID NO 9
<211> LENGTH: 422
<212> TYPE: PRT
<213> ORGANISM: Enterococcus cecorum

<400> SEQUENCE: 9

Met Val Lys Lys Arg Leu Ser Ser Val Ile Val Ser Thr Val Leu
1               5                   10                  15

Ala Gly Thr Leu Val Ala Pro Ile Ala Thr Phe Ala Asp Asn Tyr Asp
                20                  25                  30

Ser Gln Ile Glu Gln Lys Asn Ser Glu Ile Asn Asp Leu Lys Ser Lys
            35                  40                  45

Gln Ser Glu Ala Gln Asp Gln Ile Asp Arg Leu Glu Thr Ser Ile Asn
        50                  55                  60

Lys Ile Asn Lys Lys Ala Asp Glu Leu Leu Lys Glu Gln Ser Thr Leu
65                  70                  75                  80

Arg Glu Glu Thr Val Gln Leu Gln Lys Asp Ile Glu Val Leu Thr Glu
                85                  90                  95

Arg Ile Ala Lys Arg Glu Glu Ala Ile Arg Asn Gln Ala Arg Asp Val
            100                 105                 110

Gln Val Asn Asn Gln Ser Ser Val Tyr Val Lys Ala Leu Leu Asp Ala
        115                 120                 125

Thr Ser Phe Thr Asp Ala Leu Gly Arg Leu Lys Ala Met Thr Thr Ile
130                 135                 140

Val Asn Ala Asn Asn Asp Leu Val Asn Gln Gln Lys Ala Asp Lys Lys
145                 150                 155                 160

Ala Val Glu Asp Lys Lys Ala Glu Asn Glu Ala Lys Gln Glu Glu Ile
                165                 170                 175

Ala Lys Asn Gln Ala Thr Leu Glu Glu Gln Lys Gly Thr Leu Glu Ala
            180                 185                 190

Lys Gln Ala Asp Leu Asn Val Leu Lys Ala Ser Leu Ala Glu Gln Gln
        195                 200                 205

Ala Thr Lys Glu Ser Glu Lys Gln Ala Leu Ala Glu Gln Lys Ala Ala
    210                 215                 220

Phe Glu Ala Glu Gln Lys Arg Val Arg Glu Gln Gln Ala Gln Ala Ala
225                 230                 235                 240

Ala Val Gln Gln Ala Gln Gln Ala Gln Ala Ser Ala Ser Thr Ser
                245                 250                 255

Ser Asn Ala Ala Ala Ser Thr Asn Ser Asn Ala Gly Ser Ser Ser Ser
            260                 265                 270

Gln Ala Ser Ser Ser Asn Ser Ala Ser Ser Asn Ala Ser Ser Asn
        275                 280                 285

Ala Gly Val Ser Asn Val Val Ile Pro Ser Arg Pro Ala Pro Ala Pro
    290                 295                 300

Ser Gly Asn Gly Ser Ala Ile Val Ala Glu Ala Tyr Lys His Ile Gly
305                 310                 315                 320

Lys Pro Tyr Val Trp Gly Ala Lys Gly Pro Asn Thr Phe Asp Cys Ser
                325                 330                 335
```

```
Gly Phe Thr Arg Tyr Val Tyr Leu Gln Val Thr Gly Arg Asp Ile Gly
            340                 345                 350

Gly Trp Thr Val Pro Gln Glu Gly Ala Gly Ala Ile Ile Pro Val Ser
            355                 360                 365

Gln Ala Gln Pro Gly Asp Leu Tyr Phe Trp Ser Arg Gly Ser Ser
    370                 375                 380

Tyr His Val Ala Ile Ala Leu Gly Gly Gly Ser Tyr Ile His Ala Pro
385                 390                 395                 400

Gln Pro Gly Glu Ser Val Lys Val Gly Ser Val Ala Tyr Phe Ala Pro
                405                 410                 415

Ser Phe Ala Val Arg Met
            420

<210> SEQ ID NO 10
<211> LENGTH: 436
<212> TYPE: PRT
<213> ORGANISM: Enterococcus phoeniculicola

<400> SEQUENCE: 10

Met Lys Lys Ser Leu Leu Ser Thr Val Met Ile Cys Ser Leu Thr Leu
1               5                   10                  15

Thr Thr Leu Ala Ser Pro Leu Val Ala Thr Ala Asp Asn Leu Asp Asp
            20                  25                  30

Gln Ile Ala Gln Gln Asn Gln Lys Ile Ser Glu Leu Gln Gly Gln Gln
            35                  40                  45

Ala Asp Val Gln Ala Gln Ile Ser Ser Leu Gln Ala Glu Val Asp Thr
    50                  55                  60

Ile Asn Gly Lys Ala Glu Asp Leu Leu Ala Lys Gln Lys Glu Leu Tyr
65                  70                  75                  80

Thr Lys Ser Asp Glu Leu Lys Thr Glu Ile Lys Asn Leu Gln Glu Arg
                85                  90                  95

Ile Glu Lys Arg Glu Glu Ala Ile Thr Asp Gln Ala Arg Asp Val Gln
            100                 105                 110

Val Asn Gly Gly Ser Ser Asn Phe Ile Asp Ala Val Leu Asn Ala Asp
            115                 120                 125

Ser Phe Thr Asp Ala Ile Gly Arg Val Gln Ala Met Asn Thr Ile Val
    130                 135                 140

Gln Ala Asn Asn Asp Leu Val Glu Gln Gln Lys Gln Asp Lys Ala Asp
145                 150                 155                 160

Val Glu Ala Lys Glu Ala Glu Asn Lys Lys Gln Leu Glu Glu Ile Ala
                165                 170                 175

Ala Asn Gln Ala Glu Leu Glu Asn Gln Lys Gly Val Leu Thr Glu Lys
            180                 185                 190

Gln Ala Asp Leu Asn Val Leu Thr Thr Thr Leu Ala Ala Glu Gln Ala
            195                 200                 205

Thr Ala Glu Gly Lys Lys Ser Asp Leu Asn Lys Gln Lys Glu Ala Ala
    210                 215                 220

Ile Ala Glu Gln Ala Arg Val Gln Ala Glu Lys Lys Ala Glu
225                 230                 235                 240

Val Lys Ala Ala Ala Ala Glu Lys Lys Ala Glu Ala Glu Gln
                245                 250                 255

Ala Val Thr Pro Val Thr Glu Thr Gln Thr Ser Gly Asn Thr Gln Asn
            260                 265                 270

Val Val Asn Asn Asp Glu Pro Ala Lys Val Pro Glu Thr Pro Ala Ala
```

```
            275                 280                 285
Asn Ser Asn Thr Thr Ser Asn Thr Thr Pro Asn Thr Thr Pro Asp Thr
        290                 295                 300

Thr Pro Ala Glu Glu Lys Pro Val Thr Pro Thr Pro Ala Pro Ser Gly
305                 310                 315                 320

Asn Gly Ser Ser Val Val Ala Glu Ala Tyr Lys Tyr Ile Gly Thr Pro
                325                 330                 335

Tyr Val Trp Gly Gly Lys Asp Pro Ser Gly Phe Asp Cys Ser Gly Phe
            340                 345                 350

Thr Ser Tyr Val Tyr Arg Gln Ala Thr Gly Arg Glu Ile Gly Gly Trp
        355                 360                 365

Thr Val Pro Gln Glu Ser Ala Gly Ala Lys Ile Gly Ile Asn Glu Ala
    370                 375                 380

Gln Ala Gly Asp Leu Leu Phe Trp Gly Ser Pro Gly Thr His His
385                 390                 395                 400

Val Ala Ile Ala Leu Gly Gly Gly Gln Tyr Ile His Ala Pro Gln Pro
                405                 410                 415

Gly Glu Ser Val Lys Ile Gly Ser Tyr Gln Trp Tyr Ala Pro Asp Phe
            420                 425                 430

Ala Val Arg Met
        435
```

```
<210> SEQ ID NO 11
<211> LENGTH: 488
<212> TYPE: PRT
<213> ORGANISM: Enterococcus saccharolyticus

<400> SEQUENCE: 11

Met Lys Lys Arg Val Leu Thr Ala Leu Leu Thr Cys Ser Leu Thr Leu
1               5                   10                  15

Thr Ala Val Ala Ala Pro Val Ala Val Phe Ala Asp Asp Phe Asp Gln
            20                  25                  30

Gln Ile Glu Gln Lys Asn Lys Glu Ile Ser Asp Leu Gln Ala Gln Gln
        35                  40                  45

Ala Ser Ile Gln Asp Gln Ile Ser Ser Leu Glu Gly Gln Ile Ser Asp
    50                  55                  60

Ile Asn Thr Lys Ala Glu Glu Leu Ile Ala Lys Gln Gln Glu Leu Ala
65                  70                  75                  80

Ala Gln Ser Gln Lys Leu Gln Glu Glu Ile Ala Asp Leu Glu Val Arg
                85                  90                  95

Ile Glu Lys Arg Glu Glu Ala Ile Arg Lys Gln Ala Arg Asp Val Gln
            100                 105                 110

Val Asn Gly Ser Asp Ser Asn Leu Val Glu Ala Val Leu Asn Ala Asp
        115                 120                 125

Ser Leu Thr Asp Ala Ile Gly Arg Val Gln Ala Met Ser Thr Ile Val
    130                 135                 140

Asn Ala Asn Asn Glu Leu Val Asn Gln Gln Lys Glu Asp Lys Lys Ala
145                 150                 155                 160

Val Glu Thr Lys Lys Ala Glu Asn Glu Ala Lys Gln Gln Glu Ile Ala
                165                 170                 175

Glu Asn Gln Thr Ala Leu Glu Ala Gln Lys Gly Glu Ile Gln Arg Ser
            180                 185                 190

Gln Ala Asp Leu Asp Tyr Leu Lys Ala Asp Leu Ala Leu Gln Gln Ser
        195                 200                 205
```

```
Ser Lys Glu Asp Glu Lys Lys Gly Ile Gln Lys Arg Lys Ala Glu Ala
    210                 215                 220

Glu Ala Glu Arg Ala Arg Ile Ala Glu Gln Glu Arg Leu Ala Glu Leu
225                 230                 235                 240

Ala Arg Lys Ala Ala Glu Ala Ala Ala Lys Gln Ala Gln Val Glu
            245                 250                 255

Lys Glu Ala Gln Glu Ala Ala Lys Glu Gln Gln Ala Gln Val Ser Ser
            260                 265                 270

Gln Glu Gln Val Gln Ser Thr Pro Ala Thr Glu Ala Val Ala Glu
            275                 280                 285

Ser Thr Thr Glu Ala Pro Val Ala Asn Ala Thr Ser Glu Glu Pro Ala
    290                 295                 300

Ala Val Glu Thr Pro Ala Glu Thr Asn Gln Asn Thr Thr Gln Asp Thr
305                 310                 315                 320

Pro Thr Ser Thr Pro Val Val Glu Glu Lys Thr Val Glu Ser Thr Pro
                325                 330                 335

Val Gln Glu Val Val Glu Thr Pro Thr Val Glu Thr Ala Pro Val
            340                 345                 350

Glu Gln Thr Pro Val Val Glu Thr Pro Lys Val Glu Thr Pro Lys Val
            355                 360                 365

Glu Ser Ser Ala Pro Thr Gly Ser Val Val Glu Ala Tyr Lys Tyr
    370                 375                 380

Ile Gly Val Pro Tyr Val Trp Gly Gly Lys Pro Ser Gly Phe Asp
385                 390                 395                 400

Cys Ser Gly Phe Thr Ser Tyr Val Tyr Arg Lys Ala Thr Gly Arg Glu
                405                 410                 415

Ile Gly Gly Trp Thr Val Pro Gln Glu Ser Ala Gly Ser Val Ile Ser
            420                 425                 430

Val Ser Glu Ala Lys Ala Gly Asp Leu Leu Phe Trp Gly Ser Gln Gly
            435                 440                 445

Ser Thr Tyr His Val Ala Ile Ala Leu Gly Gly Gly Gln Tyr Ile His
    450                 455                 460

Ala Pro Ala Pro Gly Gln Ser Val Thr Val Ala Ser Val Ala Tyr Phe
465                 470                 475                 480

Ala Pro Ser Phe Ala Val Ser Met
                485

<210> SEQ ID NO 12
<211> LENGTH: 403
<212> TYPE: PRT
<213> ORGANISM: Enterococcus columbae

<400> SEQUENCE: 12

Met Lys Lys Arg Leu Ser Ser Val Val Ile Ala Ser Thr Val Leu Leu
1               5                   10                  15

Gly Thr Leu Thr Ala Pro Met Val Ala Met Ala Asp Asn Tyr Asp Thr
            20                  25                  30

Gln Ile Glu Gln Lys Asn Ser Glu Ile Asn Asp Leu Lys Ala Lys Gln
        35                  40                  45

Ser Ser Ala Gln Lys Gln Ile Asp Glu Leu Glu Ala Ser Val Ala Lys
    50                  55                  60

Ile Asn Lys Gln Ala Asn Glu Leu Leu Asp Gln Gln Ala Thr Leu Gln
65                  70                  75                  80

Asp Glu Ser Val Gln Leu Gln Lys Asp Ile Glu Thr Leu Lys Glu Arg
                85                  90                  95
```

Ile Ala Lys Arg Glu Glu Thr Ile Gln Arg Gln Ala Arg Asp Val Gln
            100                 105                 110

Glu Lys Asn Gln Ser Ser Val Phe Ile Lys Ala Leu Asp Ala Asp
        115                 120                 125

Ser Phe Ser Asp Ala Leu Gly Arg Leu Lys Ala Met Thr Thr Ile Val
    130                 135                 140

Asn Ala Asn Asn Asp Leu Val Asn Gln Gln Lys Ala Asp Lys Lys Ala
145                 150                 155                 160

Val Glu Asp Lys Lys Ala Glu Asn Glu Lys Lys Gln Ala Glu Ile Ala
                165                 170                 175

Ala Asn Gln Ala Lys Leu Glu Glu Gln Lys Gly Thr Leu Glu Ala Lys
            180                 185                 190

Gln Ala Asp Leu Asn Val Leu Lys Ser Thr Leu Ala Ala Gln Gln Ala
        195                 200                 205

Thr Lys Glu Ser Glu Lys Glu Ala Leu Asn Ala Gln Lys Ala Ala Tyr
    210                 215                 220

Glu Ala Glu Gln Ala Arg Ile Arg Gln Glu Gln Ala Gln Val Ala Ala
225                 230                 235                 240

Thr Arg Gln Ala Val Ala Gln Gln Ala Ser Ser Ser Gln Ala Ser Ala
                245                 250                 255

Ser Ala Ser Asn Thr Gly Ser Ser Ser Ser Ala Ser Val Ser Thr
            260                 265                 270

Pro Ala Val Ser Ile Pro Ser Thr Pro Ala Pro Ala Pro Ser Gly Asn
        275                 280                 285

Gly Ser Ala Ile Val Ala Glu Ala Tyr Lys His Ile Gly Lys Pro Tyr
    290                 295                 300

Val Trp Gly Ala Lys Gly Pro Asp Thr Phe Asp Cys Ser Gly Phe Thr
305                 310                 315                 320

Arg Tyr Val Tyr Leu Gln Val Thr Gly Arg Asp Ile Gly Gly Trp Thr
                325                 330                 335

Val Pro Gln Glu Ser Ala Gly Thr Val Ile Pro Val Ser Gln Ala Gln
            340                 345                 350

Pro Gly Asp Leu Tyr Phe Trp Gly Ser Arg Gly Ser Thr Ser His Val
        355                 360                 365

Ala Ile Ala Ile Gly Gly Gly Gln Tyr Ile His Ala Pro Gln Pro Gly
    370                 375                 380

Glu Thr Val Lys Val Gly Ser Val Ala Tyr Phe Ala Pro Ser Phe Ala
385                 390                 395                 400

Val Arg Met

<210> SEQ ID NO 13
<211> LENGTH: 525
<212> TYPE: PRT
<213> ORGANISM: Enterococcus hermanniensis

<400> SEQUENCE: 13

Met Lys Lys Ser Leu Leu Ser Ala Leu Met Val Cys Ser Val Thr Leu
1               5                   10                  15

Ser Ala Leu Ala Ala Pro Ala Ala Ser Ala Asp Glu Phe Asp Ser
            20                  25                  30

Lys Ile Ala Asp Gln Asp Ala Lys Ile Ser Ser Leu Gln Asn Gln Gln
        35                  40                  45

Thr Asp Ala Gln Ser Gln Ile Ser Ala Leu Glu Asn Glu Val Ala Ala
    50                  55                  60

```
Ile Asn Asp Gln Ala Gln Ser Leu Leu Asn Asn Gln Ala Ser Leu Arg
 65                  70                  75                  80

Gln Lys Ser Gln Asp Leu Glu Asn Gln Ile Asn Ala Leu Gln Lys Arg
                 85                  90                  95

Ile Glu Lys Arg Ser Glu Ala Ile Lys Glu Gln Ala Arg Asn Val Gln
            100                 105                 110

Val Lys Gln Ser Ser Thr Asn Val Ile Asp Val Val Leu Asn Ala Glu
            115                 120                 125

Ser Phe Ser Asp Ala Val Gly Arg Val Gln Ala Met Ser Thr Ile Val
130                 135                 140

Lys Ala Asn Asn Asp Leu Val Glu Gln Gln Lys Ala Asp Lys Ala Glu
145                 150                 155                 160

Val Glu Gln Lys Gln Ala Glu Asn Lys Lys Gln Gln Glu Ala Ile Val
                165                 170                 175

Ala Asn Gln Ser Ala Leu Glu Ser Gln Lys Gly Asp Leu Ile Thr Lys
            180                 185                 190

Gln Ala Asp Leu Asn Val Gln Thr Thr Thr Leu Ala Ala Glu Gln Ala
            195                 200                 205

Thr Ala Glu Asn Glu Lys Ala Asp Leu Gln Ala Lys Gln Glu Ala Ala
210                 215                 220

Ile Lys Glu Gln Gln Arg Val Gln Glu Ala Arg Gln Ala Ala Ala
225                 230                 235                 240

Ala Gln Glu Ala Ala Gln Lys Ala Glu Ala Glu Arg Gln Ala Gln Ala
            245                 250                 255

Asp Ala Lys Ala Gln Glu Glu Ala Ala Ser Ser Glu Ser Thr Gln
            260                 265                 270

Ala Ser Thr Glu Ala Ser Thr Thr Thr Val Glu Ser Ser Thr Thr Gln
            275                 280                 285

Glu Ser Thr Glu Ser Ser Thr Thr Val Glu Ser Ser Ser Thr Glu
            290                 295                 300

Gln Thr Ala Pro Ser Thr Ser Thr Asp Ser Ser Thr Thr Thr Glu
305                 310                 315                 320

Ser Ser Thr Ala Thr Thr Glu Asp Ser Ser Gln Ala Thr Glu Val Thr
                325                 330                 335

Pro Pro Ala Ser Ser Thr Asp Thr Ser Thr Ser Thr Asn Ser Ser
            340                 345                 350

Asn Gln Glu Ser Ser Thr Ser Thr Asn Thr Ser Thr Ser Thr Asn Asn
            355                 360                 365

Ser Ser Asn Gln Gly Ser Ser Thr Ser Thr Gly Asn Ser Asn Gln Gly
            370                 375                 380

Ser Thr Ser Ser Ser Asn Asp Gln Thr Ala Thr Thr Pro Ser Thr Pro
385                 390                 395                 400

Ser Thr Ser Thr Pro Ala Pro Ser Gly Asn Gly Ala Ala Val Val Ala
                405                 410                 415

Glu Ala Met Lys Tyr Ile Gly Thr Pro Tyr Val Trp Gly Gly Lys Thr
            420                 425                 430

Pro Ser Gly Phe Asp Cys Ser Gly Phe Thr Ala Tyr Val Tyr Arg Gln
            435                 440                 445

Ala Thr Gly Arg Glu Ile Gly Gly Trp Thr Val Pro Gln Glu Ser Ala
            450                 455                 460

Gly Thr Arg Ile Ser Val Ser Glu Ala Gln Ala Gly Asp Leu Tyr Phe
465                 470                 475                 480
```

```
Trp Gly Ser Pro Gly Gly Ser Tyr His Val Ala Ile Ala Met Gly Gly
                485                 490                 495

Gly Gln Tyr Ile His Ala Pro Gln Pro Gly Glu Ser Val Lys Val Gly
            500                 505                 510

Ser Thr Ala Tyr Tyr Ala Pro Ser Phe Ala Val Arg Met
        515                 520                 525

<210> SEQ ID NO 14
<211> LENGTH: 491
<212> TYPE: PRT
<213> ORGANISM: Enterococcus devriesei

<400> SEQUENCE: 14

Met Lys Lys Ser Leu Leu Ser Ala Leu Met Val Cys Ser Val Thr Leu
1               5                   10                  15

Ser Ala Leu Ala Ala Pro Ala Ala Ala Ser Ala Asp Glu Phe Asp Ser
            20                  25                  30

Lys Ile Ala Asp Gln Asp Ala Lys Ile Ser Ser Leu Gln Asn Gln Gln
        35                  40                  45

Thr Asp Ala Gln Ser Gln Ile Ser Ala Leu Glu Gly Glu Val Ala Ser
    50                  55                  60

Ile Asn Asp Lys Ala Gln Ser Leu Leu Asn Glu Gln Ala Thr Leu Arg
65                  70                  75                  80

Gln Lys Ser Gln Asp Leu Gln Lys Gln Ile Lys Thr Leu Gln Glu Arg
                85                  90                  95

Ile Glu Lys Arg Ser Glu Ala Ile Lys Glu Gln Ala Arg Asp Val Gln
            100                 105                 110

Val Lys Gln Ser Ser Thr Asn Val Ile Asp Val Val Leu Asn Ala Glu
        115                 120                 125

Ser Phe Ser Asp Ala Val Gly Arg Val Gln Ala Met Ser Thr Ile Val
    130                 135                 140

Lys Ala Asn Asn Asp Leu Val Glu Gln Gln Lys Ala Asp Lys Val Glu
145                 150                 155                 160

Val Glu Gln Lys Gln Ala Glu Thr Gln Lys Gln Gln Glu Gln Ile Thr
                165                 170                 175

Ala Asn Gln Ala Ala Leu Glu Ser Gln Lys Gly Asp Leu Ile Thr Lys
            180                 185                 190

Gln Ala Asp Leu Asn Val Gln Thr Thr Thr Leu Ala Ala Glu Gln Ala
        195                 200                 205

Thr Ala Glu Gly Glu Lys Ala Asn Leu Lys Asp Lys Gln Ala Ala Ala
    210                 215                 220

Ile Gln Glu Gln Gln Arg Val Gln Glu Ala Lys Lys Ala Ala Glu
225                 230                 235                 240

Ala Gln Glu Ala Ala Gln Lys Ala Glu Val Glu Arg Gln Ala Lys Ala
                245                 250                 255

Asp Ala Asp Ala Lys Ala Glu Ala Asp Arg Lys Ala Gln Glu Glu Ala
            260                 265                 270

Ala Ala Ser Ala Ser Ser Thr Glu Ser Ser Thr Val Glu Ser Ser Thr
        275                 280                 285

Thr Glu Ala Ser Ser Thr Glu Gln Thr Thr Gln Ser Ser Thr Val Glu
    290                 295                 300

Ser Ser Thr Gly Ser Thr Ser Glu Asp Asn Phe Gln Gly Gly Gly Val
305                 310                 315                 320

Thr Pro Thr Pro Thr Pro Ser Thr Thr Pro Glu Thr Pro Thr Asn
                325                 330                 335
```

```
Asn Glu Asn Ser Asn Ser Gly Asn Gln Gly Ser Asn Gln Thr Pro Ala
            340                 345                 350

Pro Thr Pro Thr Pro Thr Pro Thr Pro Glu Pro Thr Pro Ala Pro Thr
        355                 360                 365

Pro Thr Pro Ala Pro Ser Gly Asn Thr Ala Gly Val Val Ala Glu Ala
        370                 375                 380

Met Lys Tyr Ile Gly Thr Pro Tyr Val Trp Gly Lys Thr Pro Ala
385                 390                 395                 400

Gly Phe Asp Cys Ser Gly Phe Thr Ser Tyr Val Phe Arg Gln Ala Thr
                405                 410                 415

Gly Arg Glu Ile Gly Gly Trp Thr Val Pro Gln Glu Ser Ala Gly Thr
            420                 425                 430

Arg Ile Ser Val Ser Gln Ala Gln Ala Gly Asp Leu Tyr Phe Trp Gly
            435                 440                 445

Ser Pro Gly Gly Ser Tyr His Val Ala Ile Ala Met Gly Gly Gly Gln
        450                 455                 460

Tyr Ile His Ala Pro Gln Pro Gly Gln Ser Val Thr Val Ser Ser Val
465                 470                 475                 480

Ser Tyr Phe Ala Pro Ser Phe Ala Val Arg Met
                485                 490

<210> SEQ ID NO 15
<211> LENGTH: 484
<212> TYPE: PRT
<213> ORGANISM: Enterococcus malodoratus

<400> SEQUENCE: 15

Met Lys Lys Ser Leu Leu Ser Ala Leu Met Val Cys Ser Val Thr Leu
1               5                   10                  15

Ser Ala Leu Ala Ala Pro Ala Ala Ala Ser Ala Asp Glu Phe Asp Ser
                20                  25                  30

Lys Ile Ala Asp Gln Asp Ala Lys Ile Ser Ser Leu Glu Asn Gln Gln
            35                  40                  45

Thr Asp Ala Gln Ser Gln Ile Asn Ala Leu Glu Gly Glu Val Ala Ser
        50                  55                  60

Ile Asn Asp Lys Ala Gln Gly Leu Leu Asn Glu Gln Ala Ser Leu Arg
65                  70                  75                  80

Glu Lys Ser Gln Glu Leu Gln Lys Gln Ile Glu Thr Leu Asp Lys Arg
                85                  90                  95

Ile Glu Lys Arg Ser Glu Thr Ile Lys Glu Gln Ala Arg Asp Thr Gln
            100                 105                 110

Val Lys Gln Ser Ser Gly Ser Asn Val Ile Asp Val Val Leu Asn Ala
        115                 120                 125

Glu Ser Phe Thr Asp Ala Val Ser Arg Val Gln Ala Met Thr Thr Ile
130                 135                 140

Val Lys Ala Asn Asn Asp Leu Val Glu Gln Gln Lys Ala Asp Lys Ala
145                 150                 155                 160

Glu Val Glu Gln Lys Gln Ala Glu Asn Gln Lys Gln Glu Gln Ile
                165                 170                 175

Thr Ala Asn Gln Ala Thr Leu Glu Ser Gln Lys Gly Asp Leu Ile Thr
            180                 185                 190

Lys Gln Ala Asp Leu Asn Val Gln Thr Thr Thr Leu Ala Thr Gln Gln
        195                 200                 205

Ala Thr Ala Glu Ser Glu Lys Ala Ser Leu Lys Glu Lys Gln Asp Ala
```

```
            210                 215                 220
Ala Val Lys Glu Gln Gln Arg Val Gln Glu Glu Ala Arg Lys Ala Ala
225                 230                 235                 240

Glu Ala Gln Glu Ala Ala Gln Lys Ala Glu Ala Asp Arg Lys Ala Lys
                245                 250                 255

Ala Asp Ser Asp Ala Lys Ala Glu Ala Asp Arg Lys Ala Gln Glu Glu
                260                 265                 270

Ala Ala Thr Ser Thr Thr Thr Thr Glu Ser Ser Thr Ala Glu Ser Ala
                275                 280                 285

Ala Thr Val Glu Ser Ser Thr Glu Gln Gln Thr Gln Ser Ser Ala
                290                 295                 300

Thr Glu Ser Ser Ser Thr Ala Ser Thr Ser Glu Asp Asn Phe Gln Gly
305                 310                 315                 320

Gly Gly Ala Thr Pro Thr Thr Pro Ser Asp Thr Gly Asn Ser Ser Ser
                325                 330                 335

Ser Asp Gln Gly Ser Thr Ser Ser Ser Thr Asn Asn Gln Thr Pro Ser
                340                 345                 350

Thr Pro Ala Pro Thr Pro Thr Pro Thr Pro Ala Pro Ala Pro Ser Gly
                355                 360                 365

Asn Thr Gly Gly Val Val Ala Glu Ala Met Lys Tyr Ile Gly Thr Pro
370                 375                 380

Tyr Val Trp Gly Gly Lys Thr Pro Gly Gly Phe Asp Cys Ser Gly Phe
385                 390                 395                 400

Thr Ser Tyr Val Tyr Arg Gln Ala Thr Gly Arg Glu Ile Gly Trp
                405                 410                 415

Thr Val Pro Gln Glu Ser Ala Gly Thr Arg Ile Ser Val Asp Gln Ala
                420                 425                 430

Gln Ala Gly Asp Leu Tyr Phe Trp Gly Ser Pro Gly Gly Ser Tyr His
                435                 440                 445

Val Ala Ile Ala Met Gly Gly Gly Gln Tyr Ile His Ala Pro Gln Pro
                450                 455                 460

Gly Glu Thr Val Thr Val Ser Ser Val Ser Tyr Tyr Ala Pro Ser Phe
465                 470                 475                 480

Ala Val Arg Met

<210> SEQ ID NO 16
<211> LENGTH: 479
<212> TYPE: PRT
<213> ORGANISM: Enterococcus avium

<400> SEQUENCE: 16

Met Lys Lys Ser Leu Leu Ser Ala Leu Met Val Cys Ser Val Thr Leu
1               5                   10                  15

Ser Ala Leu Ala Ala Pro Ala Ala Ala Ser Ala Asp Glu Phe Asp Ser
                20                  25                  30

Lys Ile Ala Asp Gln Asp Ala Lys Ile Ser Ser Leu Gln Asn Gln Gln
            35                  40                  45

Thr Asp Ala Gln Ser Gln Ile Ser Ala Leu Glu Gly Glu Val Ala Ser
        50                  55                  60

Ile Asn Asp Lys Ala Gln Gly Leu Leu Asn Glu Gln Glu Ser Leu Arg
65                  70                  75                  80

Gln Lys Ser Gln Glu Leu Gln Lys Gln Ile Glu Thr Leu Asp Lys Arg
                85                  90                  95

Ile Glu Lys Arg Ser Glu Ala Ile Lys Glu Gln Ala Arg Asp Thr Gln
```

```
            100                 105                 110
Val Lys Gln Ser Ser Gly Thr Asn Val Ile Asp Val Leu Asn Ala
            115                 120                 125

Glu Ser Phe Thr Asp Ala Val Ser Arg Val Gln Ala Met Thr Thr Ile
            130                 135             140

Val Lys Ala Asn Asn Asp Leu Val Glu Gln Gln Lys Ala Asp Lys Ala
145             150                  155                 160

Glu Val Glu Gln Lys Gln Ala Glu Asn Lys Lys Gln Gln Gln Ile
                165                 170                 175

Ala Ala Asn Gln Ala Thr Leu Glu Ser Gln Lys Gly Asp Leu Ile Ala
            180                 185                 190

Lys Gln Ala Asp Leu Asn Val Gln Thr Thr Thr Leu Ala Ala Glu Gln
            195                 200                 205

Ala Thr Ala Glu Ser Asp Lys Ala Ser Leu Lys Glu Lys Gln Glu Ala
            210                 215                 220

Ala Ile Lys Glu Gln Gln Arg Val Gln Glu Glu Ala Arg Lys Ala Ala
225             230                 235                 240

Glu Ala Gln Glu Ala Ala Lys Lys Ala Asp Ala Glu Ala Lys Glu Lys
                245                 250                 255

Ala Asp Ala Asp Ala Lys Ala Glu Ala Asp Arg Lys Ala Gln Glu Glu
                260                 265                 270

Ala Ala Ala Ser Thr Thr Thr Glu Ser Ser Ser Ser Thr Val Glu
            275                 280                 285

Ser Ser Ser Thr Glu Gln Thr Gln Ser Ser Thr Val Asp Ser Ser Ala
            290                 295                 300

Thr Glu Ser Ser Asn Glu Asp Asn Phe Gln Gly Gly Ala Thr Pro
305             310                 315                 320

Thr Thr Pro Ser Glu Ser Gly Thr Gly Asn Thr Asn Ser Asn Asn Gln
                325                 330                 335

Gly Ser Thr Ser Ser Thr Thr Asn Asn Gln Thr Pro Ser Thr Pro Ala
            340                 345                 350

Pro Thr Pro Thr Pro Thr Pro Ala Pro Ser Gly Asn Gly Ser Gly Val
            355                 360                 365

Val Ala Glu Ala Met Lys Tyr Ile Gly Thr Pro Tyr Val Trp Gly Gly
            370                 375             380

Lys Thr Pro Ala Gly Phe Asp Cys Ser Gly Phe Thr Ser Tyr Val Phe
385             390                 395                 400

Arg Gln Ala Thr Gly Arg Glu Ile Gly Gly Trp Thr Val Pro Gln Glu
                405                 410                 415

Ser Ala Gly Thr Arg Ile Ser Val Gly Glu Ala Gln Ala Gly Asp Leu
            420                 425                 430

Tyr Phe Trp Gly Ser Pro Gly Gly Thr Tyr His Val Ala Ile Ala Met
            435                 440             445

Gly Gly Gly Gln Tyr Ile His Ala Pro Gln Pro Gly Glu Thr Val Thr
            450                 455                 460

Val Ser Ser Val Ser Tyr Tyr Ala Pro Ser Phe Ala Val Arg Met
465             470                 475

<210> SEQ ID NO 17
<211> LENGTH: 495
<212> TYPE: PRT
<213> ORGANISM: Enterococcus casseliflavus

<400> SEQUENCE: 17
```

```
Met Lys Lys Lys Ile Phe Ala Thr Val Cys Met Cys Gly Ile Val Leu
1               5                   10                  15

Ser Ser Phe Gly Gly Pro Val Thr Val Phe Ala Thr Asn His Asp Gln
            20                  25                  30

Leu Ile Glu Gln Lys Asn Asn Glu Ile Asp Gln Leu Arg Gln Gln Arg
            35                  40                  45

Gln Ser Val Gln Gly Glu Ile Asp Ser Leu Asn Gln Glu Ala Ala Ile
50                  55                  60

Ile Leu Ala Gln Gln Ser Asp Leu Leu Gln Ala Ile Glu Gly Leu Asp
65                  70                  75                  80

Gln Glu Ile Ser Gln Leu Glu Glu Arg Ile Ala Lys Arg Ser Glu Asn
                85                  90                  95

Ile Glu Lys Gln Ala Arg Glu Thr Gln Val Asn Gly Lys Gly Asp Asn
            100                 105                 110

Phe Leu Thr Ala Val Leu Glu Ala Asp Ser Val Ser Asp Leu Val Gly
            115                 120                 125

Arg Val His Ala Met Thr Thr Ile Ile Arg Ala Asn Asn Glu Val Ile
        130                 135                 140

Glu Gln Gln Lys Ala Asp Gln Gln Ala Val Glu Gln Lys Arg Ala Glu
145                 150                 155                 160

Ser Gln Glu Lys Val Ala Glu Leu Gln Ala Ala Gln Ser His Leu Glu
                165                 170                 175

Ala Gln Lys Gly Val Leu Glu Ala Ser Gln Ala Glu Leu Asn Val Leu
            180                 185                 190

Val Ser Gln Leu Ala Tyr Glu Glu Ala Thr Lys Glu Glu Lys Glu Gln
        195                 200                 205

Leu Arg Ala Glu Lys Glu Ala Tyr Glu Ala Glu Gln Ala Arg Ile Arg
210                 215                 220

Glu Glu Ala Ala Arg Val Ala Ala Leu Gln Ala Gln Ala Glu Gln Ala
225                 230                 235                 240

Ala Gln Gln Gln Ala Glu Gln Ala Ala Ala Glu Ala Ala Leu Asn
                245                 250                 255

Glu Ala Ala Val Gln Ala Glu Gly Thr Glu Ala Asp Ala Glu Ala Glu
            260                 265                 270

Ser Pro Glu Pro Ala Glu Glu Pro Ala Ala Pro Ala Glu Thr Gln Pro
        275                 280                 285

Glu Glu Thr Gln Glu Ser Glu Pro Val Glu Thr Pro Glu Ala Pro Glu
    290                 295                 300

Glu Ala Pro Val Asp Thr Pro Glu Ile Gln Glu Pro Glu Thr Pro Val
305                 310                 315                 320

Thr Pro Pro Ala Pro Glu Thr Pro Ala Asp Ser Ala Pro Ala Val Pro
                325                 330                 335

Ala Pro Thr Pro Ala Pro Thr Pro Val Thr Pro Thr Pro Ala Pro Thr
            340                 345                 350

Pro Ala Pro Ser Pro Ala Pro Ile Val Thr Pro Ala Pro Ile Val
        355                 360                 365

Thr Pro Pro Ala Pro Ser Ala Pro Ala Ser Thr Asn Gly Ala Ala Ile
    370                 375                 380

Val Ala Glu Ala Tyr Lys His Ile Gly Lys Pro Tyr Val Trp Gly Ala
385                 390                 395                 400

Lys Gly Pro Asp Ser Phe Asp Cys Ser Gly Phe Thr Arg Tyr Val Phe
                405                 410                 415

Leu Gln Val Thr Gly Arg Asp Ile Gly Gly Trp Thr Val Pro Gln Glu
```

```
                420             425             430
Thr Ala Gly Thr Val Ile Ser Val Ser Gln Ala Gln Pro Gly Asp Leu
            435             440             445

Leu Phe Trp Gly Ser Gly Ser Thr Tyr His Val Ala Ile Ala Leu
450             455             460

Gly Gly Gly Gln Tyr Ile His Ala Pro Arg Pro Gly Gln Asn Val Ser
465             470             475             480

Val Gly Ser Thr Ala His Phe Thr Pro Ser Phe Ala Val Arg Met
            485             490             495

<210> SEQ ID NO 18
<211> LENGTH: 496
<212> TYPE: PRT
<213> ORGANISM: Enterococcus gallinarum

<400> SEQUENCE: 18

Met Lys Lys Lys Ile Phe Ala Thr Val Cys Met Cys Gly Ile Val Leu
1               5                   10                  15

Ser Ser Phe Gly Gly Pro Val Thr Val Phe Ala Thr Asn His Asp Gln
            20                  25                  30

Leu Ile Glu Gln Lys Asn Asn Glu Ile Asp Gln Leu Arg Gln Gln Arg
        35                  40                  45

Gln Ser Val Gln Gly Glu Ile Asp Gly Leu Ser Ala Glu Ile Asp Ser
    50                  55                  60

Leu Asn Gln Glu Ala Ala Ile Ile Leu Ala Gln Gln Ser Asp Leu Leu
65                  70                  75                  80

Gln Ala Ile Glu Gly Leu Asp Gln Glu Ile Ser Gln Leu Glu Glu Arg
                85                  90                  95

Ile Ala Lys Arg Ser Glu Asn Ile Glu Lys Gln Ala Arg Glu Thr Gln
            100                 105                 110

Val Asn Gly Lys Gly Asp His Phe Leu Thr Ala Val Leu Glu Ala Asn
        115                 120                 125

Ser Val Ser Asp Leu Val Gly Arg Val His Ala Met Thr Thr Ile Ile
    130                 135                 140

Arg Ala Asn Asn Glu Val Ile Glu Gln Gln Lys Ala Asp Gln Gln Ala
145                 150                 155                 160

Val Glu Gln Lys Arg Ala Glu Ser Gln Glu Lys Val Ala Glu Leu Gln
                165                 170                 175

Ala Ala Gln Ser His Leu Glu Ala Gln Lys Gly Val Leu Glu Ala Ser
            180                 185                 190

Gln Ala Glu Leu Asn Val Leu Val Ser Asn Leu Ala Tyr Glu Glu Ala
        195                 200                 205

Thr Lys Glu Glu Glu Lys Glu Gln Leu Arg Ala Glu Lys Glu Ala Tyr
    210                 215                 220

Glu Ala Glu Gln Ala Arg Ile Arg Glu Ala Ala Arg Val Ala Ala
225                 230                 235                 240

Leu Gln Ala Gln Ala Glu Gln Ala Ala Gln Gln Ala Glu Gln Ala
                245                 250                 255

Ala Ala Glu Glu Ala Ala Leu Asn Glu Ala Ala Val Gln Val Glu Ser
            260                 265                 270

Thr Glu Pro Asp Val Glu Thr Glu Ser Pro Ala Pro Val Glu Glu Pro
        275                 280                 285

Glu Ala Pro Ala Glu Thr Gln Pro Glu Glu Thr Gln Glu Ser Glu Pro
    290                 295                 300
```

Val Glu Thr Pro Glu Val Pro Glu Thr Pro Val Asp Thr Pro Glu
305                 310                 315                 320

Ile His Glu Pro Glu Thr Pro Val Thr Pro Ala Thr Pro Glu Thr Pro
            325                 330                 335

Ala Asp Ser Ala Pro Ala Val Pro Ala Pro Thr Pro Ala Pro Thr Pro
            340                 345                 350

Val Thr Pro Thr Pro Ala Pro Thr Pro Ala Pro Ser Pro Ala Pro Ile
            355                 360                 365

Val Thr Pro Pro Ala Pro Ser Ala Pro Ala Ser Thr Asn Gly Ala Ala
            370                 375                 380

Ile Val Ala Glu Ala Tyr Lys His Ile Gly Lys Pro Tyr Val Trp Gly
385                 390                 395                 400

Ala Lys Gly Pro Asp Ser Phe Asp Cys Ser Gly Phe Thr Arg Tyr Val
                405                 410                 415

Phe Leu Gln Val Thr Gly Arg Asp Ile Gly Gly Trp Thr Val Pro Gln
                420                 425                 430

Glu Thr Ala Gly Thr Val Ile Ser Val Ser Gln Ala Gln Pro Gly Asp
                435                 440                 445

Leu Leu Phe Trp Gly Ser Ser Gly Ser Thr Tyr His Val Ala Ile Ala
450                 455                 460

Leu Gly Gly Gly Gln Tyr Ile His Ala Pro Arg Pro Gly Gln Asn Val
465                 470                 475                 480

Ser Val Gly Ser Thr Ala His Phe Thr Pro Ser Phe Ala Val Arg Met
                485                 490                 495

<210> SEQ ID NO 19
<211> LENGTH: 92
<212> TYPE: PRT
<213> ORGANISM: Enterococcus faecium

<400> SEQUENCE: 19

Gly Thr Pro Tyr Val Trp Gly Gly Lys Asp Pro Ser Gly Phe Asp Cys
1               5                   10                  15

Ser Gly Phe Thr Arg Tyr Val Tyr Leu Gln Val Thr Gly Arg Asp Ile
                20                  25                  30

Gly Gly Trp Thr Val Pro Gln Glu Ser Ala Gly Thr Lys Ile Ser Val
            35                  40                  45

Ser Gln Ala Lys Ala Gly Asp Leu Leu Phe Trp Gly Ser Pro Gly Gly
        50                  55                  60

Thr Tyr His Val Ala Ile Ala Leu Gly Gly Gly Gln Tyr Ile His Ala
65                  70                  75                  80

Pro Gln Pro Gly Glu Ser Val Lys Val Gly Ser Val
                85                  90

<210> SEQ ID NO 20
<211> LENGTH: 92
<212> TYPE: PRT
<213> ORGANISM: Enterococcus villorum

<400> SEQUENCE: 20

Gly Thr Pro Tyr Val Trp Gly Gly Lys Asp Pro Ser Gly Phe Asp Cys
1               5                   10                  15

Ser Gly Phe Thr Arg Tyr Val Tyr Leu Gln Val Thr Gly Arg Asp Ile
                20                  25                  30

Gly Gly Trp Thr Val Pro Gln Glu Ser Ala Gly Ala Lys Ile Ser Val
            35                  40                  45

Ser Gln Ala Lys Ala Gly Asp Leu Leu Phe Trp Ser Pro Gly Gly
        50                  55                  60

Thr Tyr His Val Ala Ile Ala Leu Gly Gly Gln Tyr Ile His Ala
65                  70                  75                  80

Pro Gln Pro Gly Glu Asn Val Lys Val Gly Ser Val
                85                  90

<210> SEQ ID NO 21
<211> LENGTH: 92
<212> TYPE: PRT
<213> ORGANISM: Enterococcus hirae

<400> SEQUENCE: 21

Gly Thr Pro Tyr Val Trp Gly Gly Lys Asp Pro Ser Gly Phe Asp Cys
1               5                   10                  15

Ser Gly Phe Thr Arg Tyr Val Tyr Leu Gln Val Thr Gly Arg Asp Ile
                20                  25                  30

Gly Gly Trp Thr Val Pro Gln Glu Ser Ala Gly Thr Lys Ile Ser Val
            35                  40                  45

Ser Gln Ala Lys Ala Gly Asp Leu Leu Phe Trp Gly Ser Ala Gly Gly
        50                  55                  60

Thr Tyr His Val Ala Ile Ser Leu Gly Gly Gly Gln Tyr Ile His Ala
65                  70                  75                  80

Pro Gln Pro Gly Glu Asn Val Lys Val Gly Ser Val
                85                  90

<210> SEQ ID NO 22
<211> LENGTH: 92
<212> TYPE: PRT
<213> ORGANISM: Enterococcus durans

<400> SEQUENCE: 22

Gly Val Pro Tyr Val Trp Gly Gly Lys Asp Pro Ser Gly Phe Asp Cys
1               5                   10                  15

Ser Gly Phe Thr Ser Tyr Val Tyr Lys Gln Val Thr Gly Arg Asp Ile
                20                  25                  30

Gly Gly Trp Thr Val Pro Gln Glu Asn Ala Gly Ala Lys Ile Ser Val
            35                  40                  45

Ser Gln Ala Lys Ala Gly Asp Leu Leu Phe Trp Gly Ser Pro Gly Gly
        50                  55                  60

Thr Tyr His Val Ala Ile Ala Leu Gly Gly Gly Gln Tyr Ile His Ala
65                  70                  75                  80

Pro Gln Pro Gly Glu Ser Val Lys Val Gly Ser Val
                85                  90

<210> SEQ ID NO 23
<211> LENGTH: 92
<212> TYPE: PRT
<213> ORGANISM: Enterococcus ratti

<400> SEQUENCE: 23

Gly Val Pro Tyr Val Trp Gly Gly Lys Asp Pro Ser Gly Phe Asp Cys
1               5                   10                  15

Ser Gly Phe Thr Arg Tyr Val Tyr Leu Gln Ala Thr Gly Arg Asp Ile
                20                  25                  30

Gly Gly Trp Thr Val Pro Gln Glu Ser Ala Gly Thr Arg Ile Ser Val
            35                  40                  45

Ser Gln Ala Lys Ala Gly Asp Leu Leu Phe Trp Gly Ser Pro Gly Gly

```
                    50                  55                  60
Ser Tyr His Val Ala Ile Ser Leu Gly Gly Gly Gln Tyr Ile His Ala
 65                  70                  75                  80

Pro Gln Pro Gly Glu Ser Val Lys Val Gly Ser Val
                 85                  90
```

<210> SEQ ID NO 24
<211> LENGTH: 92
<212> TYPE: PRT
<213> ORGANISM: Enterococcus mundtii

<400> SEQUENCE: 24

```
Gly Thr Pro Tyr Val Trp Gly Gly Lys Asp Pro Ser Gly Phe Asp Cys
  1               5                  10                  15

Ser Gly Phe Thr Arg Tyr Val Tyr Leu Gln Val Thr Gly Arg Asp Ile
                 20                  25                  30

Gly Gly Trp Thr Val Pro Gln Glu Ser Ala Gly Ala Arg Ile Ser Val
             35                  40                  45

Ser Gln Ala Lys Ala Gly Asp Leu Leu Phe Trp Gly Ala Ala Gly Gly
 50                  55                  60

Thr Tyr His Val Ala Ile Ser Leu Gly Gly Gly Gln Tyr Ile His Ala
 65                  70                  75                  80

Pro Gln Pro Gly Glu Ser Val Lys Ile Gly Ser Val
                 85                  90
```

<210> SEQ ID NO 25
<211> LENGTH: 92
<212> TYPE: PRT
<213> ORGANISM: Enterococcus hermanniensis

<400> SEQUENCE: 25

```
Gly Thr Pro Tyr Val Trp Gly Gly Lys Thr Pro Ser Gly Phe Asp Cys
  1               5                  10                  15

Ser Gly Phe Thr Ala Tyr Val Tyr Arg Gln Ala Thr Gly Arg Glu Ile
                 20                  25                  30

Gly Gly Trp Thr Val Pro Gln Glu Ser Ala Gly Thr Arg Ile Ser Val
             35                  40                  45

Ser Glu Ala Gln Ala Gly Asp Leu Tyr Phe Trp Gly Ser Pro Gly Gly
 50                  55                  60

Ser Tyr His Val Ala Ile Ala Met Gly Gly Gly Gln Tyr Ile His Ala
 65                  70                  75                  80

Pro Gln Pro Gly Glu Ser Val Lys Val Gly Ser Thr
                 85                  90
```

<210> SEQ ID NO 26
<211> LENGTH: 92
<212> TYPE: PRT
<213> ORGANISM: Enterococcus phoeniculicola

<400> SEQUENCE: 26

```
Gly Thr Pro Tyr Val Trp Gly Gly Lys Asp Pro Ser Gly Phe Asp Cys
  1               5                  10                  15

Ser Gly Phe Thr Ser Tyr Val Arg Gln Ala Thr Gly Arg Glu Ile
                 20                  25                  30

Gly Gly Trp Thr Val Pro Gln Glu Ser Ala Gly Ala Lys Ile Gly Ile
             35                  40                  45

Asn Glu Ala Gln Ala Gly Asp Leu Leu Phe Trp Gly Ser Pro Gly Gly
 50                  55                  60
```

Thr His His Val Ala Ile Ala Leu Gly Gly Gln Tyr Ile His Ala
65                  70                  75                  80

Pro Gln Pro Gly Glu Ser Val Lys Ile Gly Ser Tyr
                85                  90

<210> SEQ ID NO 27
<211> LENGTH: 92
<212> TYPE: PRT
<213> ORGANISM: Enterococcus columbae

<400> SEQUENCE: 27

Gly Lys Pro Tyr Val Trp Gly Ala Lys Gly Pro Asp Thr Phe Asp Cys
1               5                   10                  15

Ser Gly Phe Thr Arg Tyr Val Tyr Leu Gln Val Thr Gly Arg Asp Ile
                20                  25                  30

Gly Gly Trp Thr Val Pro Gln Glu Ser Ala Gly Thr Val Ile Pro Val
            35                  40                  45

Ser Gln Ala Gln Pro Gly Asp Leu Tyr Phe Trp Gly Ser Arg Gly Ser
    50                  55                  60

Thr Ser His Val Ala Ile Ala Ile Gly Gly Gln Tyr Ile His Ala
65                  70                  75                  80

Pro Gln Pro Gly Glu Thr Val Lys Val Gly Ser Val
                85                  90

<210> SEQ ID NO 28
<211> LENGTH: 92
<212> TYPE: PRT
<213> ORGANISM: Enterococcus devriesei

<400> SEQUENCE: 28

Gly Thr Pro Tyr Val Trp Gly Gly Lys Thr Pro Ala Gly Phe Asp Cys
1               5                   10                  15

Ser Gly Phe Thr Ser Tyr Val Phe Arg Gln Ala Thr Gly Arg Glu Ile
                20                  25                  30

Gly Gly Trp Thr Val Pro Gln Glu Ser Ala Gly Thr Arg Ile Ser Val
            35                  40                  45

Ser Gln Ala Gln Ala Gly Asp Leu Tyr Phe Trp Gly Ser Pro Gly Gly
    50                  55                  60

Ser Tyr His Val Ala Ile Ala Met Gly Gly Gln Tyr Ile His Ala
65                  70                  75                  80

Pro Gln Pro Gly Gln Ser Val Thr Val Ser Ser Val
                85                  90

<210> SEQ ID NO 29
<211> LENGTH: 92
<212> TYPE: PRT
<213> ORGANISM: Enterococcus malodoratus

<400> SEQUENCE: 29

Gly Thr Pro Tyr Val Trp Gly Gly Lys Thr Pro Gly Gly Phe Asp Cys
1               5                   10                  15

Ser Gly Phe Thr Ser Tyr Val Tyr Arg Gln Ala Thr Gly Arg Glu Ile
                20                  25                  30

Gly Gly Trp Thr Val Pro Gln Glu Ser Ala Gly Thr Arg Ile Ser Val
            35                  40                  45

Asp Gln Ala Gln Ala Gly Asp Leu Tyr Phe Trp Gly Ser Pro Gly Gly
    50                  55                  60

Ser Tyr His Val Ala Ile Ala Met Gly Gly Gly Gln Tyr Ile His Ala
65                  70                  75                  80

Pro Gln Pro Gly Glu Thr Val Thr Val Ser Ser Val
                85                  90

<210> SEQ ID NO 30
<211> LENGTH: 92
<212> TYPE: PRT
<213> ORGANISM: Enterococcus raffinosus

<400> SEQUENCE: 30

Gly Thr Pro Tyr Val Trp Gly Gly Lys Thr Pro Ala Gly Phe Asp Cys
1               5                   10                  15

Ser Gly Phe Thr Ser Tyr Val Tyr Arg Gln Ala Thr Gly Arg Glu Ile
                20                  25                  30

Gly Gly Trp Thr Val Pro Gln Glu Ser Ala Gly Thr Arg Ile Ser Val
                35                  40                  45

Asp Gln Ala Gln Ala Gly Asp Leu Tyr Phe Trp Gly Ser Pro Gly Gly
            50                  55                  60

Ser Tyr His Val Ala Ile Ala Met Gly Gly Gly Gln Tyr Ile His Ala
65                  70                  75                  80

Pro Gln Pro Gly Glu Thr Val Thr Val Ser Ser Val
                85                  90

<210> SEQ ID NO 31
<211> LENGTH: 92
<212> TYPE: PRT
<213> ORGANISM: Enterococcus saccharolyticus

<400> SEQUENCE: 31

Gly Val Pro Tyr Val Trp Gly Gly Lys Asp Pro Ser Gly Phe Asp Cys
1               5                   10                  15

Ser Gly Phe Thr Ser Tyr Val Tyr Arg Lys Ala Thr Gly Arg Glu Ile
                20                  25                  30

Gly Gly Trp Thr Val Pro Gln Glu Ser Ala Gly Ser Val Ile Ser Val
                35                  40                  45

Ser Glu Ala Lys Ala Gly Asp Leu Leu Phe Trp Gly Ser Gln Gly Ser
            50                  55                  60

Thr Tyr His Val Ala Ile Ala Leu Gly Gly Gly Gln Tyr Ile His Ala
65                  70                  75                  80

Pro Ala Pro Gly Gln Ser Val Thr Val Ala Ser Val
                85                  90

<210> SEQ ID NO 32
<211> LENGTH: 92
<212> TYPE: PRT
<213> ORGANISM: Enterococcus avium

<400> SEQUENCE: 32

Gly Thr Pro Tyr Val Trp Gly Gly Lys Thr Pro Ala Gly Phe Asp Cys
1               5                   10                  15

Ser Gly Phe Thr Ser Tyr Val Phe Arg Gln Ala Thr Gly Arg Glu Ile
                20                  25                  30

Gly Gly Trp Thr Val Pro Gln Glu Ser Ala Gly Thr Arg Ile Ser Val
                35                  40                  45

Gly Glu Ala Gln Ala Gly Asp Leu Tyr Phe Trp Gly Ser Pro Gly Gly
            50                  55                  60

Thr Tyr His Val Ala Ile Ala Met Gly Gly Gly Gln Tyr Ile His Ala

```
65                  70                  75                  80

Pro Gln Pro Gly Glu Thr Val Thr Val Ser Ser Val
                85                  90

<210> SEQ ID NO 33
<211> LENGTH: 92
<212> TYPE: PRT
<213> ORGANISM: Enterococcus cecorum

<400> SEQUENCE: 33

Gly Lys Pro Tyr Val Trp Gly Ala Lys Gly Pro Asn Thr Phe Asp Cys
1               5                   10                  15

Ser Gly Phe Thr Arg Tyr Val Tyr Leu Gln Val Thr Gly Arg Asp Ile
                20                  25                  30

Gly Gly Trp Thr Val Pro Gln Glu Gly Ala Gly Ala Ile Ile Pro Val
            35                  40                  45

Ser Gln Ala Gln Pro Gly Asp Leu Tyr Phe Trp Gly Ser Arg Gly Ser
    50                  55                  60

Ser Tyr His Val Ala Ile Ala Leu Gly Gly Gly Ser Tyr Ile His Ala
65                  70                  75                  80

Pro Gln Pro Gly Glu Ser Val Lys Val Gly Ser Val
                85                  90

<210> SEQ ID NO 34
<211> LENGTH: 92
<212> TYPE: PRT
<213> ORGANISM: Enterococcus gilvus

<400> SEQUENCE: 34

Gly Thr Pro Tyr Val Trp Gly Gly Lys Thr Pro Ala Gly Phe Asp Cys
1               5                   10                  15

Ser Gly Phe Thr Ser Tyr Val Phe Arg Gln Ala Thr Gly Arg Glu Ile
                20                  25                  30

Gly Gly Trp Thr Val Pro Gln Glu Ser Ala Gly Thr Arg Ile Ser Val
            35                  40                  45

Gly Glu Ala Gln Ala Gly Asp Leu Tyr Phe Trp Gly Ser Pro Gly Gly
    50                  55                  60

Thr Tyr His Val Ala Ile Ala Met Gly Gly Gly Gln Tyr Ile His Ala
65                  70                  75                  80

Pro Gln Pro Gly Glu Thr Val Thr Val Ser Ser Val
                85                  90

<210> SEQ ID NO 35
<211> LENGTH: 92
<212> TYPE: PRT
<213> ORGANISM: Enterococcus casseliflavus

<400> SEQUENCE: 35

Gly Lys Pro Tyr Val Trp Gly Ala Lys Gly Pro Asp Ser Phe Asp Cys
1               5                   10                  15

Ser Gly Phe Thr Arg Tyr Val Phe Leu Gln Val Thr Gly Arg Asp Ile
                20                  25                  30

Gly Gly Trp Thr Val Pro Gln Glu Thr Ala Gly Thr Val Ile Ser Val
            35                  40                  45

Ser Gln Ala Gln Pro Gly Asp Leu Leu Phe Trp Gly Ser Ser Gly Ser
    50                  55                  60

Thr Tyr His Val Ala Ile Ala Leu Gly Gly Gly Gln Tyr Ile His Ala
65                  70                  75                  80
```

```
Pro Arg Pro Gly Gln Asn Val Ser Val Gly Ser Thr
                85                  90

<210> SEQ ID NO 36
<211> LENGTH: 92
<212> TYPE: PRT
<213> ORGANISM: Enterococcus gallinarum

<400> SEQUENCE: 36

Gly Lys Pro Tyr Val Trp Gly Ala Lys Gly Pro Asp Ser Phe Asp Cys
1               5                   10                  15

Ser Gly Phe Thr Arg Tyr Val Phe Leu Gln Val Thr Gly Arg Asp Ile
            20                  25                  30

Gly Gly Trp Thr Val Pro Gln Glu Thr Ala Gly Thr Val Ile Ser Val
        35                  40                  45

Ser Gln Ala Gln Pro Gly Asp Leu Leu Phe Trp Gly Ser Ser Gly Ser
    50                  55                  60

Thr Tyr His Val Ala Ile Ala Leu Gly Gly Gly Gln Tyr Ile His Ala
65                  70                  75                  80

Pro Arg Pro Gly Gln Asn Val Ser Val Gly Ser Thr
                85                  90
```

MODIFIED MICROORGANISMS EXPRESSING SAGA AND RELATED COMPOSITIONS FOR IMMUNOMODULATION AGAINST INFECTION AND CANCER IMMUNOTHERAPY

CROSS-REFERENCE TO RELATED APPLICATIONS

This application is the U.S. National Stage Application of International Patent Application No. PCT/US2020/019038, filed Feb. 20, 2020, which claims the benefit of U.S. Provisional Application Ser. No. 62/807,830, filed Feb. 20, 2019, the disclosures of which are hereby incorporated by reference in their entirety, including all figures, tables and amino acid or nucleic acid sequences.

STATEMENT REGARDING FEDERALLY SPONSORED RESEARCH

This invention was made with government support under contract no. R01 GM103593 awarded by the National Institutes of Health. The government has certain rights in the invention.

The Sequence Listing for this application is labeled "Seq-List.txt" which was created on Feb. 20, 2020 and is 90 KB. The entire content of the sequence listing is incorporated herein by reference in its entirety.

FIELD

The present disclosure relates generally to use of naturally occurring and recombinant microorganisms expressing secreted antigen A (SagA) proteins as anti-infective agents, as well as for use in stimulating immune responses and potentiating vaccine and anti-cancer agents.

BACKGROUND

Cancer remains a significant health burden and is the second leading cause of mortality in the U.S. and worldwide, with an estimated 9.6 million deaths globally in 2018. However, the disease results from a myriad of different causes with quite variable genotypes and drug susceptibilities, requiring the development of many targeted therapies and individualized treatment regimens. Fortunately, cancer immunotherapies such as immune checkpoint inhibitors (ICIs) have exhibited broad success in the clinic against diverse cancer types. For example, six separate antibodies targeting PD-1/PD-L1 have been approved by the FDA to treat melanoma, Hodgkin's lymphoma, renal cell carcinoma, hepatocellular carcinoma, cervical, non-small-cell lung, colorectal, gastric, kidney, bladder, head and neck cancers and others. Moreover, anti-PD-1/PD-L1 drugs are currently being tested in single or combination therapy in over 2,250 active clinical trials as of September 2018, underscoring both the great potential and wide impact of these novel immunotherapies. Nevertheless, not all patients respond to ICIs, and the underlying determinants that distinguish non-responding versus responding patients remain unclear. Thus, identifying mechanisms that alter the efficacy of ICI therapies is an ongoing need. In this regard, commensal microbes within the human gut play a critical role in the efficacy of immunotherapies and other cancer drugs, including anti-CTLA4 and anti-PD-1/PD-L1, indicating that the gut microbiota is a necessary component of immunotherapeutic modes of action. Although these and other studies correlate the microbiota composition and cancer immunotherapy response, the causative factors from the microbiota that lead to improved drug efficacy are unknown. Thus, there is an ongoing and unmet need to provide new and improved compositions and methods that can harness the benefit of microbiota on immunotherapy and other outcomes. The present disclosure is pertinent to this need.

BRIEF DESCRIPTION OF THE DRAWINGS

FIG. 1. Representative orthologs of *Enterococcus faecium* secreted antigen A (SagA).

FIG. 2. Full sequences of representative SagA orthologs.

FIG. 3. C-terminal NlpC/p60 domains of SagA orthologs (Inter-Pro) and Percent ID (MView, EMBL-EBI).

FIG. 4A) Abx-pretreated specific-pathogen-free (SPF) mice are colonized with different *Enterococcus* strains, inoculated with B16/F10 cells and evaluated for tumor growth, alterations in immune responses and microbiota composition. FIG. 4B) Tumor growth of $1\times10^5$ B16/F10 cells injected into C57BL/6 mice with or without anti-PD-L1 treatment and Enterococci colonization (n=8 per condition, mean±s.e.m.).

FIG. 5A) Schematic of SagA-like proteins from Efm, Edr and Ehr with percent identity compared to Efm SagA domains. FIG. 5B) Western blot of SagA from different *Enterococcus* species.

FIG. 6A) Schematic summary of wild-type and mutant SagA-His6 constructs expressed in Lpl. FIG. 6B) Expression and secretion levels of wild-type and mutant SagA-His6 constructs expressed in Lpl. FIG. 6C) Survival curve of *C. difficile* infected mice. Mice were treated for 7 days with Abx cocktail and then orally gavaged with PBS or $5\times10^8$ CFU of *L. plantarum* (Lpl) containing empty vector or a vector expressing a SagA variant followed by Cdf infection. Pooled data from 3 independent experiments, n=9-10 mice/group.

FIG. 7A) Tumor growth of $3\times10^5$ MC-38 cells injected into C57BL/6 mice with or without anti-CTLA-4 treatment and Enterococci colonization (n=8 per condition, mean±s.e.m.). FIG. 7B) Tumor growth of $6\times10^5$ MCA205 cells injected into C57BL/6 mice with or without anti-PD-1 treatment and Enterococci colonization (n=8 per condition, mean±s.e.m.).

FIGS. 8A-8C. SagA sequence identity, SagA expression and tumor growth model in C57BL/6 mice to evaluate different Enterococci strains. FIG. 8A) Western blot of SagA from different *Enterococcus* strains. FIG. 8B) Colonization of gastrointestinal tract by different *Enterococcus* species. FIG. 8C) Tumor growth of $1\times10^5$ B16/F10 cells injected into C57BL/6 mice with anti-PD-1 treatment and/or Enterococci colonization of different Enterococci spp. (n=8 per condition, mean±s.e.m.).

FIG. 9A) Colonization of gastrointestinal tract by different *Enterococcus* species. FIG. 9B) Tumor growth of $1\times10^5$ B16/F10 cells injected into SPF-Taconic mice with anti-PD-L1 treatment and Enterococci colonization (n=8 per condition, mean±s.e.m.).

FIG. 10A) Individual tumor growth of 1×10$^5$ B16/F10 cells injected into NOD2$^{-/-}$ and NOD2$^{+/-}$ mice with anti-PD-L1 treatment and Enterococci colonization (n=8 per condition). FIG. 10B) Mean tumor growth of 1×10$^5$ B16/F10 cells injected into NOD2$^{-/-}$ and NOD2$^{+/-}$ mice with anti-PD-L1 treatment and Enterococci colonization (n=8 per condition, mean±s.e.m.).

FIG. 12A illustrates the number of surviving mice and FIG. 12B illustrates the weight of the mouse each day, unless the mouse was euthanized before the 10 days expired.

BRIEF DESCRIPTION OF SEQUENCES

Figures 4A, 4B:
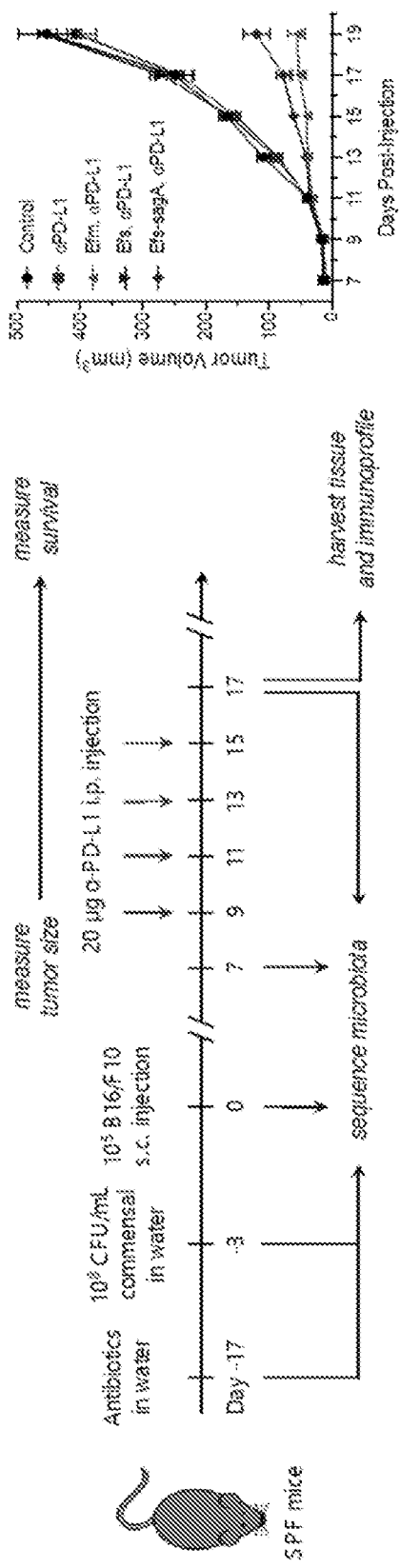
FIGS. 4A-4B. Tumor growth model in C57BL/6 mice to evaluate Enterococci strains during PD-L1 therapy.

SEQ ID NO: 1 is the protein sequence of the heterologous SagA.
SEQ ID NOs: 2-18 are sequences of representative SagA orthologs.
SEQ ID NOs: 19-36 are sequences of C-terminal NlpC/p60 domains of SagA orthologs (Inter-Pro) and Percent ID (MView, EMBL-EBI).

DETAILED DESCRIPTION OF THE INVENTION

As used herein, the singular forms "a", "an" and "the" are intended to include the plural forms as well, unless the context clearly indicates otherwise. Furthermore, to the extent that the terms "containing", "including", "includes", "having", "has", "with", or grammatical variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" or "approximately" means within an acceptable error range for the particular value as determined by one of ordinary skill in the art, which will depend in part on how the value is measured or determined, i.e., the limitations of the measurement system. The terms "about" and "approximately" are meant to encompass a range of 20%, ±10% or ±5% of a given value. Thus, in the context of compositions containing amounts of ingredients where the terms "about" or "approximately" are used, these compositions can contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

The terms "simultaneous" or "simultaneously" as applied to the method of treating an individual with cancer using SagA refers to adding one or more components to the subject at the same time, or at two different time points that are separated by no more than 3 minutes. The phrase "after or before" as applied to methods of treating an individual with cancer refers to providing more than one composition at two different time points that are separated by more than 3 minutes, e.g., about 5 minutes, 30 minutes, 1 hour, about 2 hours, about 5 hours, or even longer.

The present disclosure is based in part on our discovery that *Enterococcus faecium* can activate host immunity and inhibit pathogenesis by various strains of bacteria, and also function to enhance certain anti-cancer approaches.

The disclosure includes all amino acid sequences described herein, and all polynucleotides encoding the amino acid sequence. The disclosure also includes all amino acid sequences that have at least 80% similarity to any amino acid sequence described herein. The percent amino acid sequence can be determined across the full length of any amino acid sequence described herein, or across any contiguous amino acid sequence that constitutes a functional domain, such as a NlpC/p60 domain, non-limiting examples of which are provided below. As such, the disclosure includes sequences that are the same as any amino acid sequence described herein, and from 80, 81, 82, 83, 84, 85, 86, 87, 88, 89, 90, 91, 92, 93, 94, 95, 96, 97, 98, 99% identical to such sequences. Likewise, the disclosure includes each type of bacteria described herein, and all combinations of such bacteria, and compositions comprising said bacteria and bacteria combinations, and methods comprising administering such bacteria and bacteria combinations to an individual, with or without vaccine or immune checkpoint inhibitor, as further described below. In one aspect the present disclosure provides a modified microorganism, such as modified bacteria, wherein the organism expresses a heterologous SagA. A "heterologous" SagA protein is a SagA protein that is not normally encoded by the genome of the microorganism. Accordingly, heterologous SagA production involves introducing a SagA-encoding DNA sequence into the microorganism. The modified microorganism comprises a heterologous SagA coding sequence, the expression of which is driven by a promoter operative in the microorganism. The SagA protein can be expressed from any suitable expression vector or other construct introduced into the microorganism. In embodiments the heterologous SagA is encoded by a plasmid introduced into the modified microorganism, or is encoded by a segment of DNA introduced into a bacterial chromosome. In embodiments, the SagA encoded by modified bacteria is a truncated and/or mutated SagA, which may be referred to as a SagA component.

Many reagents and methods for introducing and expressing any heterologous gene in a wide variety of microorganisms are known in the art and are suitable for use with the present invention. In general, the disclosure contemplates microorganisms that are modified to express and secrete heterologous SagA that retains the ability to generate peptidoglycan fragments from a suitable peptidoglycan-containing substrate. In one embodiment, the recombinantly produced SagA protein comprises the amino acid sequence:

```
                                                 (SEQ ID NO: 1)
MKKSLISAVMVCSMTLTAVASPIAAAADDFDSQIQ

QQDQKIADLKNQQADAQSQIDALESQVSEINTQAQ

DLLAKQDTLRQESAQLVKDIADLQERIEKREDTIQ

KQAREAQVSNTSSNYIDAVLNADSLADAIGRVQAM

TTMVKANNDLMEQQKQDKKAVEDKKAENDAKLKEL

AENQAALESQKGDLLSKQADLNVLKTSLAAEQATA

EDKKADLNRQKAEAEAEQARIREQQRLAEQARQQA

AQEKAEKEAREQAEAEAQATQASSTAQSSASEESS

AAQSSTTEESSSAAQSSTTEESTTAPESSTTEEST

TAPESSTTEESTTVPESSTTEESTTVPESSTTEES

TTVPESSTTEESTTVPETSTEESTTPAPTTPSTDQ

SVDPGNSTGSNATNNTTNTTPTPTPSGSVNGAAIV

AEAYKYIGTPYVWGGKDPSGFDCSGFTRYVYLQVT

GRDIGGWTVPQESAGTKISVSQAKAGDLLFWGSPG

GTYHVAIALGGGQYIHAPQPGESVKVGSVQWFAPD

FAVSM,
``` or a sequence that has at least 80% identity to this sequence, provided such non-identical sequences retain NlpC/p60-type hydrolase activity. In this representative sequence, the NlpC/p60 hydrolase domain is from amino acid 389 through amino acid 530. In embodiments, other *E. faecium* SagA sequences are known and would be expected to function in place of Com15 SagA, the sequence of which is given above. In embodiments, the SagA protein is from any of the following types of bacteria, and the disclosure includes any amino acid sequence that has at least 80% identity to such SagA sequences, provided non-identical sequences retain NlpC/p60-type hydrolase activity that are listed in FIGS. 1, 2 and 3. The polynucleotide and amino acid sequences from each database entry stated in this disclosure are incorporated herein as they exist on the filing date of this application or patent.

In embodiments, the SagA protein is modified so that it has, for example, additional or fewer amino acids than in the sequence presented above. In non-limiting examples, the SagA protein is modified to include additional amino acids used for isolation, purification, or detection, including but not necessarily limited to amino acid residues in the C-terminus, or a polypeptide sequence that is capable of producing a detectable signal, such as a fluorescent signal.

In embodiments, the disclosure includes modified bacteria that express heterologous SagA protein, with the proviso that the gram-negative bacteria do not include *Escherichia coli*. In embodiments, the disclosure includes modified bacteria that are facultative anaerobes. In embodiments the modified bacteria are gram-positive and gram-negative bacteria that express heterologous SagA protein. In embodiments the gram-positive bacteria are members the *Lactobacillus* genus, and in particular *Lactobacillus* species that are active in the production of food products intended for human and/or non-human animal consumption. In non-limiting embodiments the modified bacteria are *Lactobacillus* species that are active in the production of dairy products, such as yogurt, milk, milk-based creams, ice cream products, and cheese, or fermented drinks, such as wine, cider and beer, or fermented foods, or combinations of the foregoing. In certain embodiments the modified bacteria are *L. plantarum, L. casei, L. acidophilus, L. salivarius*, or *L. reuteri* as well as probiotic strains of *Lactococcus lactis* and *Bifidobacterium* (e.g., *B. longum*).

In embodiments, the disclosure includes combinations of modified bacteria described herein, and further comprises combinations of the modified bacteria with other microorganisms, such as yeasts. Those skilled in the art will recognize that such combinations are useful for production of certain foods.

In another aspect, the disclosure comprises a food product comprising modified bacteria that expresses a heterologous SagA protein. Such products include all of the aforementioned types of food and modified bacteria, and may further include modified bacteria that express a heterologous SagA. In embodiments the food product is a dairy product, including but not necessarily limited to yogurt, milk, milk-based creams, and cheese. Use of microorganisms in making foods that intentionally contain live cultures, such as yogurts, are well known in the art and can be adapted for use with the presently provided modified microorganisms. In one aspect the food product is a non-human animal feed, such as food intended for consumption by a bovine, equine, canine, porcine, feline, avian or reptilian animal, or by aquatic animals such as fish. In certain aspects the food product comprises packaging, such as a paper or cardboard carton, plastic container, bottle, bag, etc., that are well known for containing foods. The packaging can provide printed material which includes information that identifies the modified bacteria present in the food product.

In another aspect, the disclosure includes a supplement product, such as a nutraceutical product, a dietary supplement, a food ingredient, etc., including but not limited to a probiotic formulation or functional food that contains one or more live modified bacteria as described herein. The supplement product can be provided in the form of, for example, a liquid, capsules, tablets, soft gels, powders, freeze-dried compositions, and the like.

In another aspect, the disclosure provides a pharmaceutical composition comprising modified microorganisms and/or isolated or purified recombinant SagA as described herein. The pharmaceutical composition can include any suitable diluent, carrier, excipient, buffer, etc., intended for use with the microorganisms for prophylactic and/or therapeutic human or veterinary purposes. Some examples of compositions suitable for preparing pharmaceutical compositions can be found in: Remington: The Science and Practice of Pharmacy (2005) 21st Edition, Philadelphia, Pa. Lippincott Williams & Wilkins. Such compositions may also be included in supplement products.

In an embodiment the disclosure includes making modified bacteria that express heterologous SagA for use in inhibiting bacterial infections, or for maintaining or modifying the intestinal flora of an individual. The method comprises introducing into bacteria a heterologous SagA encoding DNA sequence, and culturing the bacteria for use as a probiotic, nutraceutical or pharmaceutical agent. In embodiments, the disclosure comprises such bacterial cultures themselves, and further includes such cultures scaled for use in producing nutraceutical, probiotic and/or pharmaceutical preparations. In embodiments, the cultures are propagated as, for example, a yogurt culture. The disclosure also includes composition and methods that employ bacteria that are unmodified, at least with respect to their expression of SagA or a SagA ortholog, non-limiting examples of such SagA orthologs being presented in FIGS. 1-3. In embodiments, the bacteria express a SagA ortholog that comprises an amino acid sequence that is at least 80% identical to the SagA-NlpC/p60 hydrolase domain, non-limiting examples of which are shown at least in FIG. 3. In embodiments, a composition comprising only a single type or strain of bacteria is provided and/or administered to an individual. In embodiments, a mixture of distinct types/strains of bacteria is provided and/or is administered to an individual.

In another aspect, the disclosure includes a method comprising introducing into modified bacteria, wherein the modified bacteria expresses a heterologous SagA. The modified bacteria can be introduced as a component of a food product, a probiotic formulation, or a pharmaceutical formulation. In an aspect the disclosure includes a method for prophylaxis and/or therapy of a bacterial infection in an individual. The method comprises administering to an individual in need a composition comprising isolated SagA, or a bacterial population wherein at least some members of the population have been modified to produce SagA. In another approach, the composition can comprise peptidoglycan fragments generated by SagA. Compositions and uses thereof comprising combinations of peptidoglycan fragments generated by SagA, modified bacteria that express SagA and isolated SagA are also encompassed by this disclosure. Compositions of the disclosure may be used prophylactically when they are given to an individual prior to exposure to pathologic bacteria, or within a short time, i.e., several hours, after exposure to pathologic bacteria. Therapeutic approaches comprise administering the engineered bacteria to an individual who has or is suspected of having a bacterial infection, wherein the severity of the infection is lessened subsequent to the administration.

In embodiments, administering a composition to an individual for, for instance, prophylaxis and/or therapy of a bacterial infection according to this disclosure can be performed using any suitable approach. In one embodiment, the composition is consumed by the individual as a probiotic formulation, or as a component of a food item and is thus introduced orally. In another embodiment the composition is administered as a pharmaceutical formulation. The pharmaceutical formulation can be administered using any suitable route, including but not necessarily limited to parenteral, intraperitoneal, intrapulmonary, oral, intra-abdominal, and others. Parenteral infusions include intramuscular, intravenous, intraarterial, intraperitoneal, and subcutaneous administration.

The amount of modified bacteria, SagA, and any other active agent to be included in a composition and/or to be used in the method can be determined by those skilled in the art, given the benefit of the present disclosure. Thus, in one embodiment, an effective amount of a composition is administered. An effective amount can be an amount of the composition that inhibits growth of bacterial cells in the individual, or reduces a sign or symptom of bacterial infection. In embodiments, the individual to whom a composition of the invention is administered has, is suspected of having, or is at risk for development of a bacterial infection. In embodiments, the bacterial infection is an infection by enteric pathogens such as strains of *Salmonella, Escherichia coli, Shigella, Campylobacter, Helicobacter, Francisella, Vibrio, Yersinia, Enterococcus*, Clostridia and pathogenic strains of microbiota. In embodiments, a composition of this disclosure is administered to an individual such that the growth of enteric pathogens in the individual is inhibited, and/or the amount of enteric pathogens is reduced, or the enteric pathogens are eradicated.

Suitable dosages for either therapeutic or prophylactic purposes can be determined by those skilled in the art and will be based, at least in part, on consideration of the individual's age, sex, size, and health, the type of bacterial infection, and other factors as will be apparent to the skilled artisan. In embodiments, a composition of the invention can be administered in combination with an antibiotic.

In one aspect, the disclosure relates to methods for cancer therapy comprising administering to an individual in need a combination of an immune checkpoint inhibitor (ICI) and one or more SagA proteins, fragments thereof, and/or one or more types of bacteria that express SagA or a derivative thereof or bacteria that express heterologous SagA (collectively referred to herein as "SagA components").

In embodiments, the individual in need of treatment in accordance with this disclosure is any mammal, including but not limited to a human. The cancer type is not particularly limited, other than being a cancer type for which immune checkpoint inhibition may be a suitable prophylactic and/or therapeutic approach. In embodiments, the individual is at risk for, is suspected of having, or has been diagnosed with a cancer. In embodiments, the cancer is melanoma, lung, colon, breast, pancreatic, brain, liver, bladder, kidney, melanoma, ovary, testicular, esophageal, gastric, fibrosarcoma, rhabdomyosarcoma, head and neck, renal cell, thyroid, or a blood cancer.

The disclosure is also pertinent to approaching cancers that are or may become resistant to treatment with one or more immune checkpoint inhibitors. Thus, in certain implementations the individual has been previously treated for cancer with a checkpoint inhibitor but was not treated with a SagA component while being treated with the checkpoint inhibitor; and, the cancer was initially resistant, or develops resistance, to the checkpoint inhibitor treatment. The disclosure thus includes selecting an individual who has cancer that is resistant to a checkpoint inhibitor as a monotherapy, and administering to the individual a checkpoint inhibitor and a SagA component, as described herein. The individual who is resistant to a checkpoint inhibitor as a monotherapy accordingly means an individual who was administered a checkpoint inhibitor for the cancer but was not also administered a SagA component; and, the cancer was resistant to the treatment that included the checkpoint inhibitor but not the SagA component. The monotherapy may have included other anti-cancer agents or other interventions, so long as such other agents did not include a SagA component that is subsequently used in a combination therapy of this disclosure. In one embodiment the individual who is treated with a combination approach described herein has never been previously treated with a SagA component. In certain embodiments, the individual who is treated with a combination therapy of this disclosure has not been diagnosed with, is not suspected of having, or is not a risk for developing a non-cancerous condition for which a SagA component would be prescribed.

In certain embodiments, a combination of an immune checkpoint inhibitor and a SagA component exerts a synergistic effect against cancer, which may comprise but is not limited to a greater than additive inhibition of cancer progression, and/or a greater than additive inhibition of an increase in tumor volume, and/or a reduction in tumor volume, and/or a reduction in tumor growth rate, and/or an eradication of a tumor and/or cancer cells. The method may also result in a prolonging of the survival of the individual.

The disclosure also comprises monitoring the treatment of an individual who is receiving a combination of an immune checkpoint inhibitor and a SagA component. This approach comprises administering the combination of an immune checkpoint inhibitor and a SagA component as a cancer treatment, testing the individual and/or a biological sample from the individual to determine the efficacy of the combination therapy, and if determined to be necessary, adjusting the combination therapy by, for example, changing the amount of the immune checkpoint inhibitor or the a SagA component, or both, and/or changing the type of immune checkpoint inhibitor and or the a SagA component. Retesting and changing the combination therapy may also be performed.

The immune checkpoint inhibitor used in combination with the one or more SagA components described herein can be any immune checkpoint inhibitor. As is known in the art, an example of an immune checkpoint is the transmembrane programmed cell death 1 protein (PDCD1, PD-1; also known as CD279) and its ligand, PD-1 ligand 1 (PD-L1, CD274). In normal, non-malignant physiology, PD-L1 on the surface of a cell binds to PD-1 on the surface of an immune cell, which inhibits the activity of the immune cell. PD-L1 up-regulation on cancer cell surfaces is thought to facilitate evasion of the host immune system, at least in part by inhibiting T cells that would otherwise target the tumor cell. In alternative embodiments, other immune checkpoints can be inhibited, such as CTLA-4.

In embodiments, any one or more checkpoint inhibitors can be combined with any one or more SagA components described herein for use in the methods of this disclosure. In certain embodiments, the checkpoint inhibitors that are combined with the SagA component comprise antibodies that bind to PD-1, or anti-PD-L1, such as nivolumab, pembrolizumab, durvalumab, atezolizumab, and avelumab. In another embodiment, the checkpoint inhibitor is an antibody that targets CTLA-4, such as ipilimumab and tremelimumab. In another embodiment the checkpoint inhibitor is targets CD366 (Tim-3), which is a transmembrane protein also known as T cell immunoglobulin and mucin domain containing protein-3.

In alternative embodiments, the checkpoint inhibitors comprise small molecules or other agents that disrupt the immune checkpoint that is exploited by cancer cells to evade cell-mediated or other immune-mediated targeting.

Those skilled in the art, given the benefit of the present disclosure, will recognize how to determine an effective amount of the combination of checkpoint inhibitor and a SagA component for treatment of cancer. In general, and without intending to be bound by any particular theory, it is expected that the amounts of each checkpoint inhibitors that are used and/or tested currently in humans for their separate indications will also be effective in the presently provided combination approach. But modifications can be made by medical professionals based on known conditions, such as the size, age, gender and overall health profile of the individual, the type and stage of the cancer, and other conditions and risk factors that will be otherwise apparent to those skilled in the art. In embodiments, administering the checkpoint inhibitor and a SagA component has a greater than additive effect on tumor inhibition, relative to use of either agent alone. A greater than additive effect can be determined by comparing the effects of one or both of the agents to any suitable reference, including but not limited to a predetermined value.

In embodiments, one or more SagA components and one or more immune checkpoint inhibitors are administered concurrently. In embodiments, the one or more SagA components and one or more immune checkpoint inhibitors are combined into a single pharmaceutical formulation. In embodiments, the one or more SagA components and the one or more immune checkpoint inhibitors are administered sequentially. The SagA components and immune checkpoint inhibitor can be administered via any suitable route, including but not necessarily limited to intravenous, intramuscular, subcutaneous, oral, and parenteral routes.

In an embodiment, the combination therapy has a greater than additive inhibition of tumor growth, which may be determined using any suitable measurement, non-limiting examples of which include determining tumor volume or tumor growth rate. The combination therapy can be combined with any other, conventional cancer therapies, including but not limited to surgical and chemotherapeutic approaches.

In alternative embodiments, one or more SagA components described herein are administered in combination with immunotherapy regimens, such as T-cell transfer therapy, antibodies targeting different cancers, a cancer vaccine, and/or immune system modulators. Methods of T-cell transfer therapy are well-known in the art, including tumor infiltrating lymphocytes therapy and CAR T-cell therapy. Antibodies, such as the antibodies available on the IMGT monoclonal antibody database website (see Worldwide Website: imgt.org/mAb-DB), can be administered to a patient in need of treatment of cancer. A cancer vaccine can also be used to treat cancer in an individual. In addition to administering antibodies to immune checkpoint inhibitors, other immune system modulators can be used including cytokines, such as interferons and interleukins, or immunomodulatory drugs, such as thalidomide, lenalidomide, pomalidomide, or imiquimod. The following description and specific Example is provided to illustrate the invention, but are not intended to be limiting in any way.

EXAMPLES

A greater understanding of the present invention and of its many advantages may be had from the following examples, given by way of illustration. The following examples are illustrative of some of the methods, applications, embodiments, and variants of the present invention. The examples are not to be considered as limiting the invention.

Example 1—SagA is Sufficient to Improve Efficacy of Immune Checkpoint Inhibitor Antibodies This example pertains to specific microbial and host factors involved in Enterococci-mediated improvement of ICI therapy to exploit host-microbiota interactions during cancer immunotherapy and develop new ICI therapeutic approaches.

In particular, and as alluded to above, based on our data in mammalian cells and mouse models, embodiments of this disclosure include use of *Enterococcus faecium* (Efm) and other SagA-expressing *Enterococcus* species to improve cancer immunotherapy efficacy through their unique peptidoglycan composition and remodeling activity. In this regard, Enterococci and immunotherapy efficacy remains mostly correlative, and individual species have not been directly evaluated during cancer immunotherapy treatment.

In embodiments, these effects are tested using in vivo tumor models, immune profiling and microbiota analysis upon colonization with individual *Enterococcus* species to provide new protective factors/pathways for cancer treatment. For example, the analysis of Enterococci SagA provides a basis for development of engineered probiotics to enhance cancer immunotherapy. In connection with this, it has already been demonstrated that SagA can be expressed in the probiotic species *Lactobacillus plantarum* (Lpl) and confer protective activity against intestinal pathogens (see, for example, PCT publication WO 2016/172476), highlighting how beneficial commensal bacteria factors may be successfully transferred into existing probiotic strains.

In non-limiting embodiments, the disclosure includes assessing, using non-limiting examples of SagA-expressing Enterococci, to assess whether colonization is sufficient to improve anti-PD-L1, anti-CTLA-4, or anti-PD-1 efficacy. In embodiments, the well-established tumor growth model with B16/F10 syngeneic melanoma cells, MC-38 adenocarcinoma cells, or MCA205 fibrocarcinoma cells in C57BL/6 mice is used to illustrate certain approaches of this disclosure. For this approach, in a non-limiting example, six- to ten-week-old male and female mice are first treated with an antibiotic (Abx) cocktail (1 g/L ampicillin, 1 g/L colistin sulfate and 5 g/L streptomycin) for 14 days to deplete the endogenous microbiota and facilitate colonization by *Enterococcus* species.

On the day prior to administration, bacteria were inoculated into 4 mL of autoclaved growth medium and grown as overnight cultures. On the following day, overnight cultures were used to inoculate 50 mL of growth medium at a dilution ratio of 1:50. Bacteria were grown to late logarithmic phase (OD~1), centrifuged at 5,000×g for 10 min, and then resuspended in sterile-filtered drinking water. Bacteria were then diluted in two 50-mL aliquots per animal cage in sterile conical tubes to $10^8$ CFU/mL as previously determined by dilution plating. Tubes were then fitted with autoclaved #6 sipper tubes and provided to the animals ad libitum. For *Enterococcus* strains and species, the bacterial solutions were replaced at least twice weekly. For *Lactococcus lactis* strains, solutions were replaced every other day. Supplemented drinking water was maintained throughout the remainder of the experiment. As controls, separate cohorts are inoculated with the non-protective species *Enterococcus faecalis* (Efs, strain OG1RF) or vehicle only.

After 24 h, the animals are then subcutaneously injected with either B16/F10 melanoma cells, MC-38 adenocarcinoma cells, or MCA205 fibrocarcinoma cells. B16/F10 and MCA205 cells were cultured at 37° C. and 5% $CO_2$ in complete DMEM (ThermoFisher, 11995065) supplemented with 10% fetal bovine serum, 100 μg/mL penicillin, and 100 μg/mL streptomycin. MC-38 cells were cultured at 37° C. and 5% $CO_2$ in the medium described above supplemented with 0.1 mM non-essential amino acids. The final amount of injected cells for each cell type is as follows: B16/F10—1×$10^5$ cells; MC-38-3×$10^5$ cells; MCA205—6×$10^5$ cells.

Tumor growth is quantified by digital calipers two to three times per week for a period of time, such as at least 2.5 weeks.

Starting on day 9 post-injection, mice are intraperitoneally (i.p.) injected with antibodies, such as every two days for four total injections. The antibodies and amount per injection used are as follows: 20 μg anti-PD-L1 (BioXCell, clone 10F.9G2—20 or 100 μg; anti-PD-1 (BioXCell, BP0146)—100 μg; anti-CTLA-4 (BioXCell, BP0131)—100 μg. As a negative control, one of the vehicle-inoculated cohorts is i.p. injected with the antibody dilution buffer. Survival may be measured, with endpoints defined as the first of >20% weight loss, 1 $cm^3$ tumor volume, tumor necrosis, or visual signs of distress or pain. All tumor growth experiments can be statistically analyzed by linear mixed modeling. Survival is estimated by Kaplan-Meier, and survival curves are analyzed by log rank test corrected for multiple comparisons (FIG. 4A).

Experiments indicate that Efn and Efs-sagA, but not Efs can inhibit tumor growth after anti-PD-L1 treatment (FIG. 4B). Data presented herein indicate that heterologous expression of SagA in otherwise inactive bacteria (Efs) can significantly improve anti-PD-L1 therapy in a murine model of melanoma (FIG. 4B).

Figure 7A:
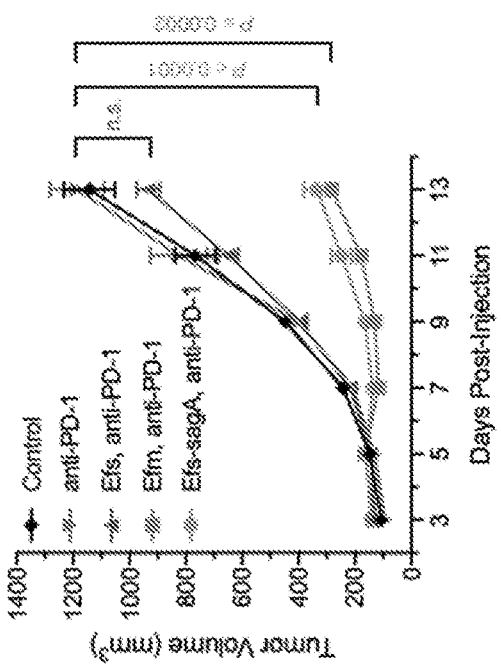
FIGS. 7A-7B. Tumor growth model in C57BL/6 mice to evaluate Enterococci strains naturally or recombinantly expressing SagA during anti-CTLA-4 or anti-PD-1 immunotherapy.
Figure 7B:
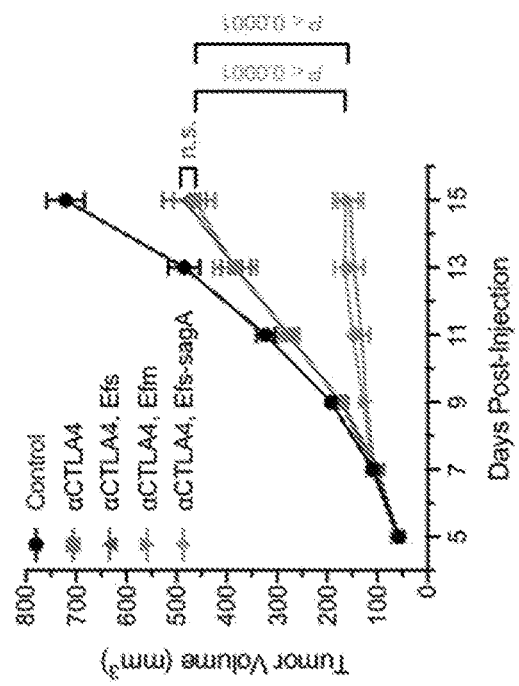

Experiments indicated that Efn and Efs-sagA, but not Efs can inhibit tumor growth after anti-CTLA-4 treatment in a murine model of colon adenocarcinoma (FIG. 7A). Similarly, experiments indicated that Efn and Efs-sagA, but not Efs can inhibit tumor growth after anti-PD-1 treatment in a murine model of fibrosarcoma (FIG. 7B). The data presented indicate that heterologous expression of SagA can significantly improve anti-CTLA-4 and anti-PD-1 therapies in murine models.

Example 2—SagA Orthologs are Present Throughout the *Enterococcus* Genus

Figure 5A:
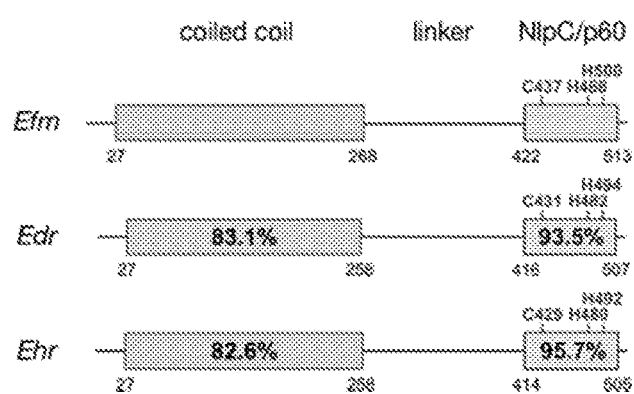
FIGS. 5A-5B. SagA sequence identity, SagA expression and peptidoglycan profile of Enterococci species.
Figure 5B:
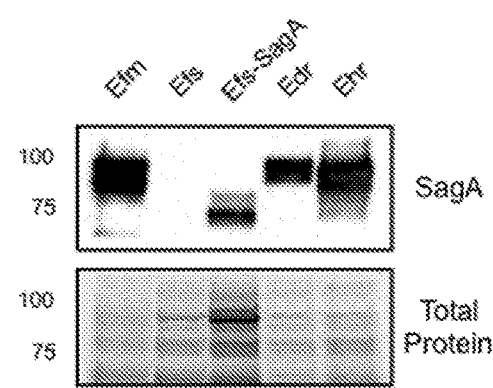

Comparative genomic analysis between other Enterococci species and Efs suggests that immunotherapy-associated Enterococci species express unique bacterial adhesion, metabolism and peptidoglycan remodeling. Remarkably, amongst these uniquely expressed genes, our previously characterized peptidoglycan hydrolase SagA is highly conserved across these strains at the protein level (FIG. 5A). More detailed sequence analysis shows that Edr and Ehr contained SagA-like orthologs with high conservation in the C-terminal NlpC/p60 catalytic hydrolase domain of Efm SagA (FIG. 5A). To confirm the expression of SagA orthologs in Edr, Eds, Ehe, Emi, Egm, and Ehr, overnight cultures of each strain were separately grown along with Efm, Efs-sagA and Efs as positive and negative controls, respectively. Western blotting with a polyclonal antibody against Efm SagA recently generated in our lab showed robust signal in Edr and Ehr (FIG. 5B) and in Efm, Eds, and Ehe (FIG. 8A), demonstrating that Efm SagA-like proteins are produced and secreted in other *Enterococcus* strains. Our studies show that Efm and Efs-sagA, but not Efs, can enhance anti-PD-L1, anti-CTLA-4, and anti-PD-1 activities against tumor growth (FIG. 4B, FIG. 7A, and FIG. 7B, respectively). Additionally, Eds and Ehe can enhance anti-PD-L1 activity against tumor growth (FIG. 8C).

Importantly, many *Enterococcus* spp. (Efm, Efs, Eds, Ehe, Emi, Egm) are able to colonize the gastrointestinal tract of the mouse (FIG. 8B). This was investigated by determining the CFU/g of feces. Fecal samples were sterilely collected three days after the start of *Enterococcus* spp. administration. Samples were weighed, resuspended in sterile PBS, homogenized by grinding with sterile pestles, serially diluted in sterile PBS, and then plated by drip assay onto selective BD BBL Enterococcosel agar plates (Fisher Scientific, B12205). Plates were incubated for 24-48 h at 37° C. under ambient atmospheric pressure until colonies formed. Colonies were then manually counted to determine the results found in FIGS. 8B and 9B.

These results indicate that SagA-like NlpC/p60 hydrolases in Enterococci species may be a significant determinant of their ICI enhancing activity. It will be recognized that results presented herein indicate that SagA expression in Enterococci may be involved in enhancing ICI efficacy and that SagA orthologs are also present in the other ICI response-associated Enterococci species (FIGS. 1 and 2). The disclosure thus includes the use of Enterococci species that express SagA orthologs with 80 percent protein identity to SagA-NlpC/p60 domain (FIG. 3), listed above as immunomodulators to prevent pathogen infection, adjuvants for vaccine development or in combination with ICI for cancer therapy.

Figures 6A, 6B, 6C:
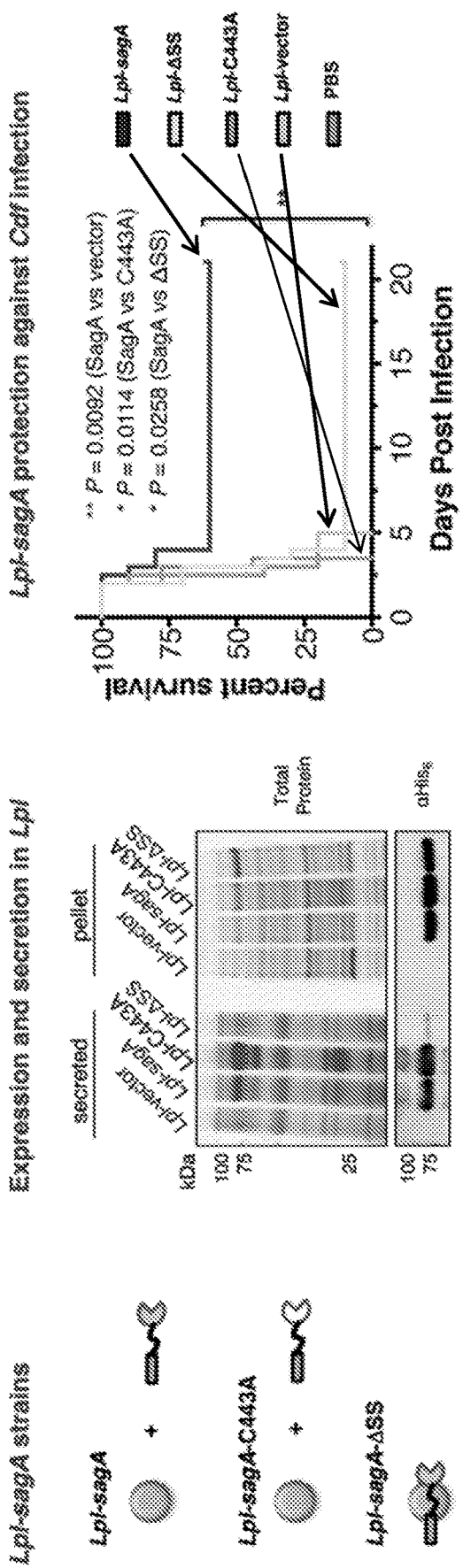
FIGS. 6A-6C. Activity of Lpl-sagA strains against Cdf infection in mice.

Example 3—SagA Expression and Secretion in *Lactobacillus Plantarum* and *Lactococcus Lactis* Confers Protection Against Pathogens The presently provided discovery of Efm SagA activity, its conservation in other ICI-associated Enterococci strains, and its ability to maintain activity upon transfer to other bacteria as illustrated above provide a unique opportunity to engineer and improve existing probiotics for ICI treatment. As discussed above, it has already been demonstrated that SagA can be expressed in the probiotic species *Lactobacillus plantarum* (Lpl) and confer protective activity against intestinal pathogens in vivo. Furthermore, we recently demonstrated that SagA secretion and catalytic activity are required for this protective activity in vivo. In a murine model of *Clostridium difficile* infection, Lpl strains expressing SagA signal sequence (Lpl-ΔSS) and active site (Lpl-C443A) mutants were inactive compared to Lpl expressing wild-type SagA (Lpl-sagA, FIG. 6C).

Figure 12A:
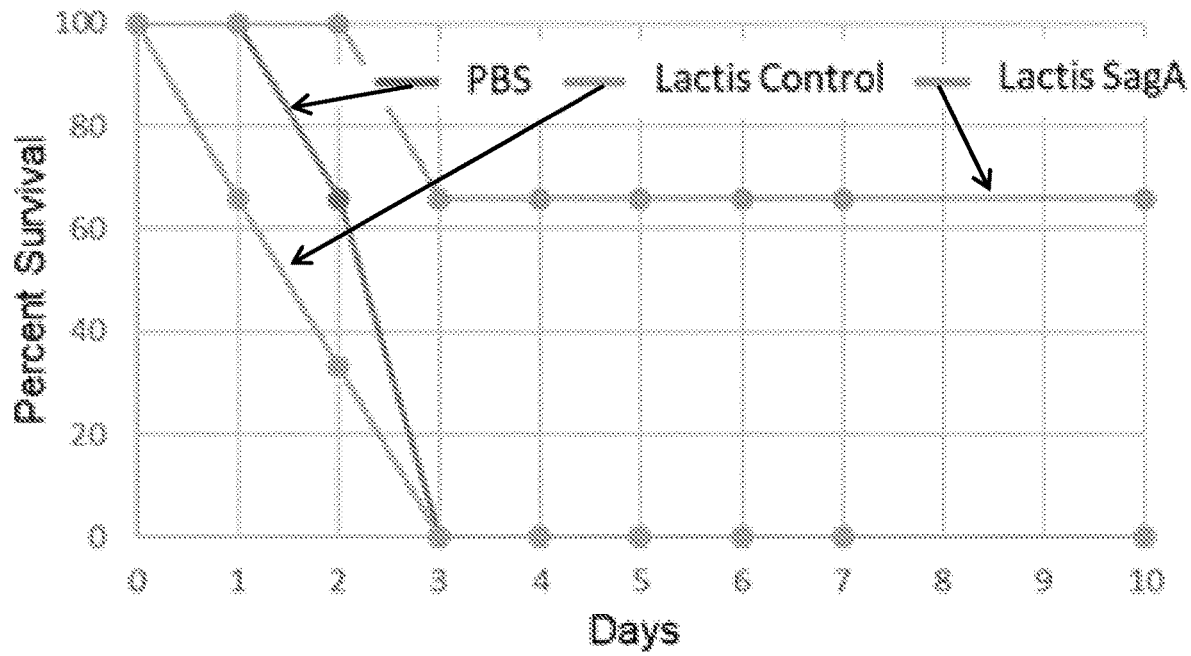
FIGS. 12A-12B. *L. lactis* expressing heterologous SagA protects against survival in a murine *C. difficile* infection model. To establish the *C. difficile* infection model, mice were gavaged with the AMNV (4 mg ampicillin, 2 mg metronidazole, 4 mg neomycin, 2 mg vancomycin) antibiotic cocktail daily for 7 days before receiving an oral administration of clindamycin (10 mg/kg). Two days later mice (8/group) were treated by oral gavage with phosphate-buffered saline (PBS), 1×10$^9$ CFU of negative control *L. lactis* MG1363 (Lactis Control), or 1×10$^9$ CFU of *L. lactis* expressing SagA (Lactis SagA). Mice were then infected with *C. difficile* 30 hours after treatment.
Figure 12B:
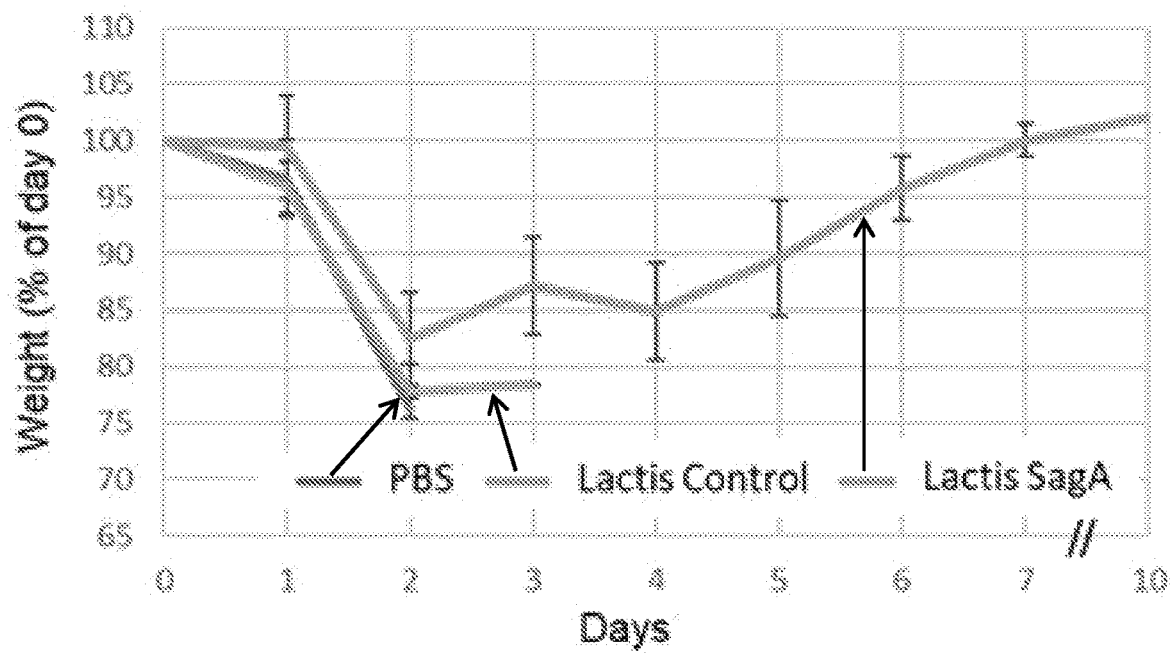

To test the efficacy of *L. lactis* SagA in an acute model of *C. difficile* infection, C57BL/6J mice 8 weeks of age were purchased from the Jackson Laboratory and gavaged with the AMNV (4 mg ampicillin, 2 mg metronidazole, 4 mg neomycin, 2 mg vancomycin) antibiotic cocktail daily for 7 days before receiving an oral administration of clindamycin (10 mg/kg). Two days later, mice (8/group) were orally administered one of the following: vehicle phosphate-buffered saline (PBS), $1 \times 10^9$ CFU of a negative control strain of *L. lactis* (Lactis Control), or $1 \times 10^9$ CFU of *L. lactis* expressing SagA (Lactis SagA). Mice were then infected with *C. difficile* 30 hours after treatment. Weight loss was monitored before and during infection for up to 10 days. Mice were euthanized when they reached 80% baseline weight or when they appeared hunched or moribund, whichever occurred first. As shown in the FIG. 12A, *L. lactis* SagA protected mice from infection compared to the PBS-treated (vehicle control) animals or Lactis Control-treated animals, which all died within 3 days of the *C. difficile* initial infection. *L. lactis* SagA treated animals showed some weight loss initially but then began regaining weight after day 3 and by day 10 were back to original weight levels (FIG. 12B). Thus, *L. lactis* expressing heterologous SagA effectively protected mice against *C. difficile* infection.

These results support a variety of uses of SagA secretion and extracellular cleavage of peptidoglycan fragments in vivo, and further demonstrate SagA-expression and activity is sufficient to improve ICI efficacy in the B16/F10 melanoma model described in Example 1. Further, as discussed in Example 2, the disclosure includes use of other Enterococci SagA orthologs and SagA variant for heterologous expression and secretion in the probiotics. In addition to the naturally occurring variants of SagA, the disclosure includes structural variants such as the SagA-NlpC/p60 domain alone with signal sequence, which is more catalytically active than the purified full-length SagA in vitro as well as rationally engineered SagA variants. While the invention has been described through specific embodiments, routine modifications will be apparent to those skilled in the art and such modifications are intended to be within the scope of the present invention.

Example 4—SagA Expression can Treat Immunotherapy Non-Responsive Microbiota In Vivo In non-limiting embodiments, the disclosure includes assessing, using non-limiting examples of SagA-expressing Enterococci, to assess whether colonization is sufficient to reprogram non-response microbiota for cancer immunotherapy. In certain embodiments, the well-established tumor growth model with B16/F10 syngeneic melanoma cells in SPF-Taconic mice (which have a less responsive microbiota) is used to illustrate certain approaches of this disclosure and an antibiotic mixture was not used to modify the microbiota of SPF-Taconic mice. However, similar to the protocol of Example 1, on the day prior to administration, *Enterococcus* spp. were inoculated into 4 mL of autoclaved growth medium and grown as overnight cultures, diluted to a ratio of 1:50, grown to late logarithmic phase, and then resuspended in sterile-filtered drinking water. Bacteria were then diluted in two 50-mL aliquots per animal cage. Tubes were provided to the animals ad libitum. As controls, separate cohorts are inoculated with the non-protective species *Enterococcus faecalis* (Efs, strain OG1RF) or vehicle only. After 24 h, the animals are then subcutaneously injected with cultured B16/F10 melanoma cells. Tumor growth is quantified by digital calipers. Starting on day 9 post-injection, mice are intraperitoneally (i.p.) injected with), such as every two days for four total injections.

Figure 9A:
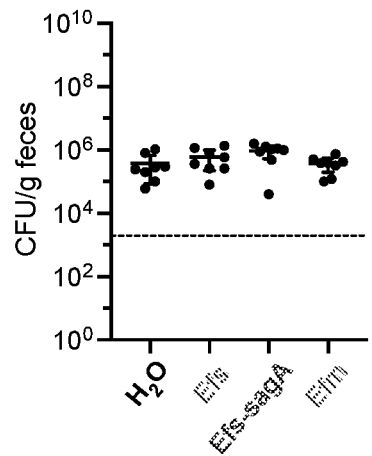
FIGS. 9A-9B. Tumor growth model in SPF-Taconic mice to evaluate Enterococci strains during ICI therapy in an organism with a non-responsive microbiota.
Figure 9B:
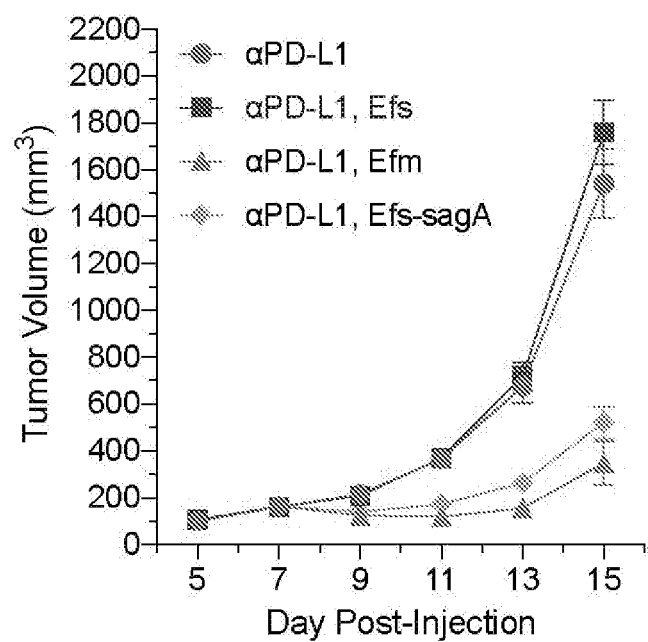

Experiments indicated that Efm and Efs-sagA, but not Efs can inhibit tumor growth after anti-PD-L1 treatment in a murine model of melanoma with a less responsive microbiota (FIG. 9B). Efs, Efs-sagA, and Efm are all able to colonize the gastrointestinal tract of the SPF-Taconic mice (FIG. 9A). The methods used to determine colonization are explained in Example 2. The data presented indicate that heterologous expression of SagA can significantly improve anti-PD-L1 therapies in murine models of melanoma with less responsive microbiotas.

Example 5—Nod2 is Required for SagA-Mediated Anti-Tumor Immunotherapy

In non-limiting embodiments, the disclosure includes assessing, using non-limiting examples of SagA-expressing Enterococci, to assess whether Nod2 is required for SagA-mediated cancer immunotherapy. In certain embodiments, the well-established tumor growth model with B16/F10 syngeneic melanoma cells in NOD2$^{-/-}$ mice (The Jackson Laboratory, 005763) is used to illustrate certain approaches of this disclosure. Similarly to the protocol of Example 1, mice are first treated with an antibiotic (Abx) cocktail. On the day prior to administration, *Enterococcus* spp. were inoculated into 4 mL of autoclaved growth medium and grown as overnight cultures, diluted to a ratio of 1:50, grown to late logarithmic phase, and then resuspended in sterile-filtered drinking water. Bacteria were then diluted in two 50-mL aliquots per animal cage. Tubes were provided to the animals ad libitum. As controls, separate cohorts are inoculated with the non-protective species *Enterococcus faecalis* (Efs, strain OG1RF) or vehicle only. After 24 h, the animals are then subcutaneously injected with cultured B16/F10 melanoma cells. Tumor growth is quantified by digital calipers. Starting on day 9 post-injection, mice are intraperitoneally (i.p.) injected with), such as every two days for four total injections.

Figure 10A:
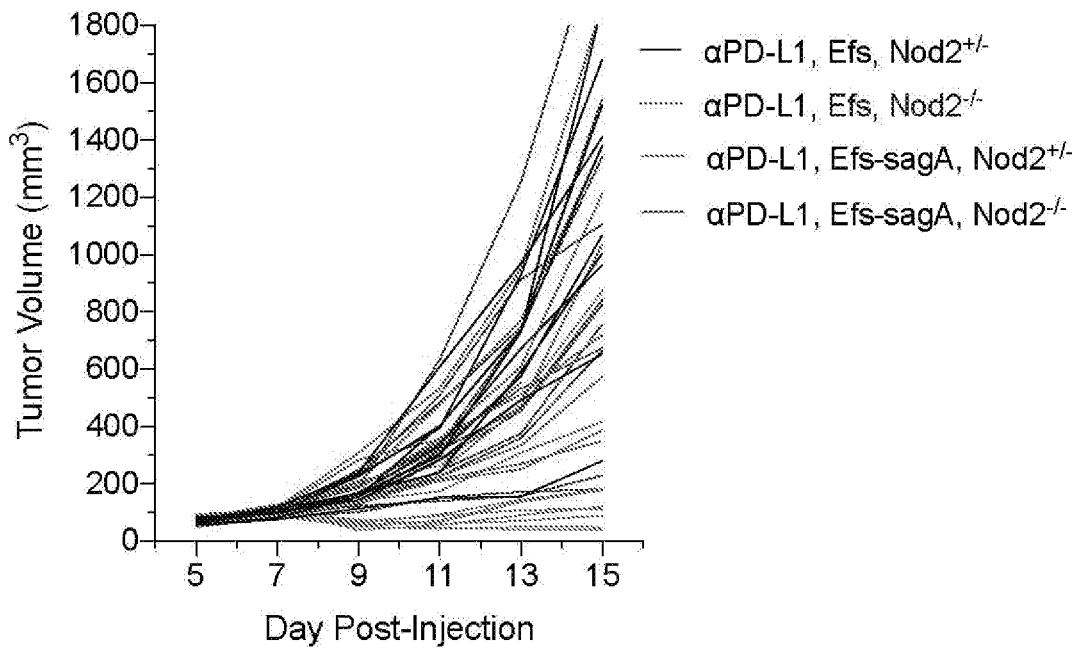
FIGS. 10A-10B. Tumor growth model in NOD2$^{-/-}$ and NOD2$^{+/-}$ mice to evaluate the role of Nod2 during ICI therapy.
Figure 10B:
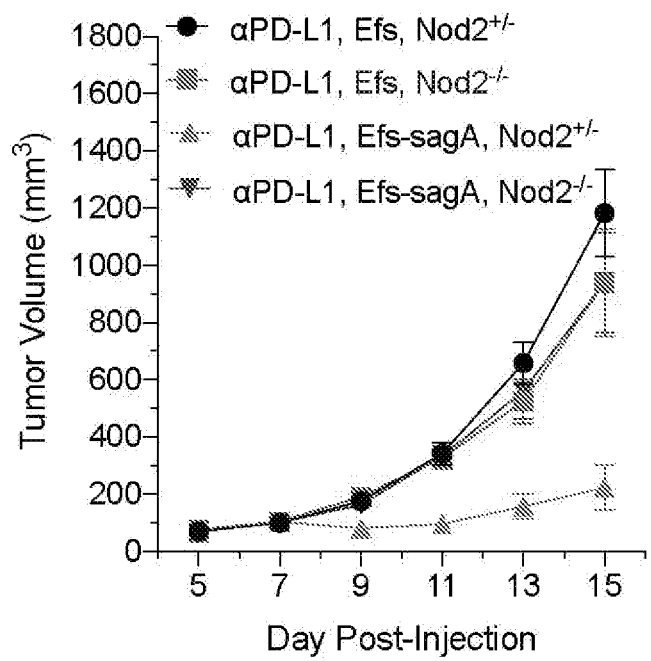

Experiments indicated that neither Efs-sagA nor Efs can inhibit tumor growth after anti-PD-L1 treatment in a NOD2$^{-/-}$ murine model of melanoma (FIGS. 10A and 10B). However, Efs-sagA significantly inhibits tumor growth NOD2$^{+/-}$ murine model of melanoma when compared to Efs-sagA in a NOD2$^{-/-}$ murine model of melanoma (FIGS. 10A and 10B). The data presented indicate that heterologous expression of SagA can significantly improve anti-PD-L1 therapies in murine models of melanoma only if Nod2 is present.

Figure 11:
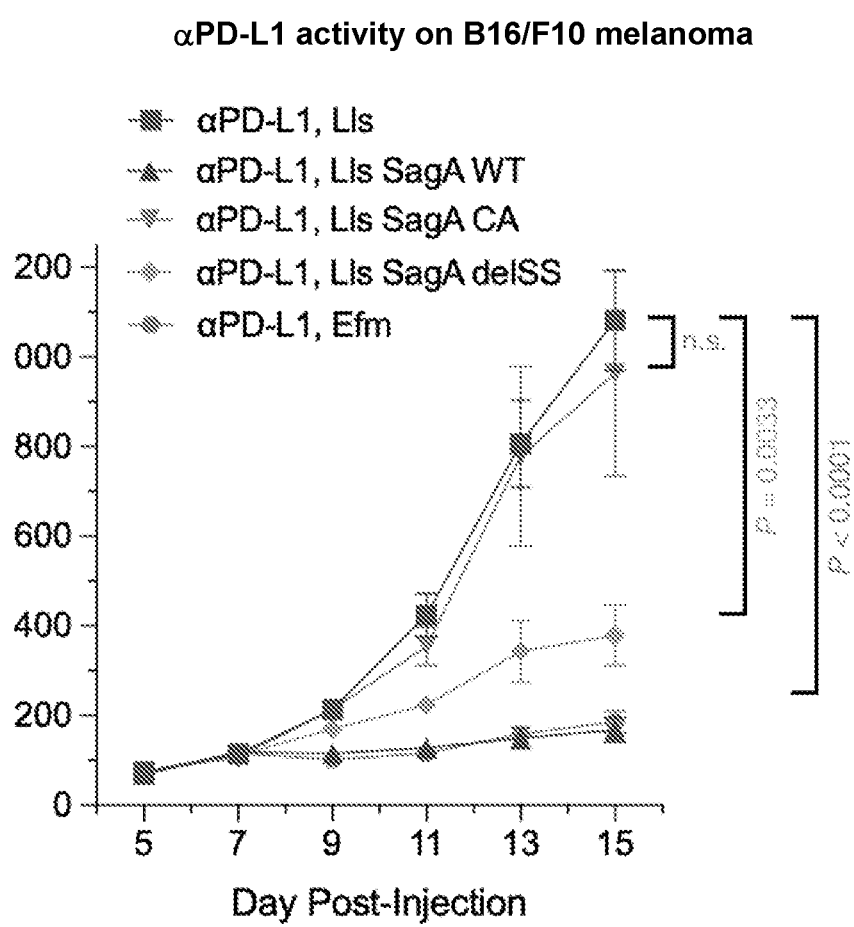
FIG. 11. SagA-*L. lactis* restores immune checkpoint inhibitor efficacy. *L. lactis* (Lls) lines express either wild-type SagA (Lls WT), catalytically inactive SagA (Lls CA), or SagA variant that does not contain the signal sequence and is not secreted (Lls delSS). Mean tumor growth of 1×10$^5$ B16/F10 cells injected into C57BL/6 mice with anti-PD-L1 treatment and Lls, Lls WT, Lls CA, Lls delSS, or Efm dosing (n=8 per condition).

Example 6—*L. lactis* Expressing Heterologous SagA Restores Immune Checkpoint Inhibitor Efficacy The ability for various, genetically modified *L. lactis* strains to restore immune checkpoint inhibitor efficacy was tested; the various *L. lactis* strains have either a wild-type SagA (Lls WT), a catalytically inactive version of SagA with a mutation at residue 384 that abolishes hydrolase activity (Lls CA), or a signal sequence deletion version which eliminates SagA cellular (Lls delSS). Animals were fed 10$^9$ CFU/ml of each strain in the context of the B16/F10 murine tumor model methods discussed in Example 1. For this study, tumor growth was quantified by digital calipers every other day on days 5-15. All tumor growth experiments were statistically analyzed by linear mixed modeling. While tumors grew at a rapid and consistent rate for the group treated with anti-PD-L1 and *L. lactis*, the group treated with *L. lactis* expressing WT SagA (Lls WT) demonstrated profound anti-tumor activity, which was similar to *E. faecium* (which naturally expresses SagA) when combined with anti-PD-L1 treatment (FIG. 11). In contrast, the catalytically inactive *L. lactis* SagA (Lls CA) demonstrated no anti-tumor activity, and the *L. lactis* line expressing the deleted signal peptide sequence and deficient for secretion of SagA (Lls delSS) demonstrated a statistically significant anti-tumor effect but not as robust as Lls WT (FIG. 11). Thus, the results demonstrated the ability for SagA expressed by *L. lactis* to restore checkpoint inhibitor efficacy.

While the invention has been described through specific embodiments, routine modifications will be apparent to those skilled in the art and such modifications are intended to be within the scope of the present invention.

We claim:

1. Modified bacteria comprising that express a heterologous secreted antigen A (SagA) or an ortholog of SagA, said heterologous SagA having at least 80% sequence identity to SEQ ID NO: 1 and said ortholog having a NlpC/p60 hydrolase domain having at least 80% sequence identity to SEQ ID NO: 19, wherein the modified bacteria are *Lactococcus lactis*.

2. The modified bacteria of claim 1, wherein the heterologous SagA is *Enterococcus faecium* SagA, or a SagA ortholog from: *Enterococcus durans, Enterococcus hirae, Enterococcus mundtii, Enterococcus raffinosus, Enterococcus gilvus, Enterococcus villorum, Enterococcus ratti, Enterococcus cecorum, Enterococcus phoeniculicola, Enterococcus saccharolyticus, Enterococcus columbae, Enterococcus hermanniensis, Enterococcus devriesei, Enterococcus malodoratus, Enterococcus avium, Enterococcus casseliflavus*, or *Enterococcus gallinarum*.

3. The modified bacteria of claim 2, wherein the bacteria express an ortholog of the heterologous SagA that has greater than 80% and less than or equal to 89% sequence identity to SEQ ID NO: 19.

4. The modified bacteria of claim 1, wherein the bacteria express a heterologous SagA that has greater than 80% and less than or equal to 89% sequence identity to SEQ ID NO: 1.

5. A food product for human or non-human animal consumption comprising the modified bacteria of claim 1.

6. The food product of claim 5, wherein the food product is a dairy product.

7. A probiotic formulation comprising the modified bacteria of claim 1.

* * * * *